(12) United States Patent  (10) Patent No.: US 8,562,572 B2
Proulx et al.  (45) Date of Patent: Oct. 22, 2013

(54) DISPOSABLE, STERILE FLUID TRANSFER DEVICE

(75) Inventors: Stephen Proulx, Boxboro, MA (US); Joseph Almasian, Westford, MA (US); Naren Renganath, Burlington, MA (US); Stephen Tingley, North Reading, MA (US); Martin Morrissey, Beverly, MA (US)

(73) Assignee: EMD Millipore Corporation, Billerica, MA (US)

( * ) Notice: Subject to any disclaimer, the term of this patent is extended or adjusted under 35 U.S.C. 154(b) by 1460 days.

(21) Appl. No.: 11/350,384

(22) Filed: Feb. 8, 2006

(65) Prior Publication Data
US 2006/0142730 A1 Jun. 29, 2006

Related U.S. Application Data

(62) Division of application No. 10/500,077, filed as application No. PCT/US03/12927 on Apr. 25, 2003, now Pat. No. 7,927,316.

(60) Provisional application No. 60/375,747, filed on Apr. 26, 2002.

(51) Int. Cl.
*A61M 5/00* (2006.01)

(52) U.S. Cl.
USPC .................. 604/249; 604/533; 604/319

(58) Field of Classification Search
USPC ........... 604/533, 537, 249; 251/319, 324, 325
See application file for complete search history.

(56) References Cited

U.S. PATENT DOCUMENTS

| | | | |
|---|---|---|---|
| 214,367 A | 4/1879 | Colvin |
| 988,378 A | 4/1911 | Olson |
| 1,503,132 A | 7/1924 | Prator |
| 1,585,163 A | 5/1926 | Milner |

(Continued)

FOREIGN PATENT DOCUMENTS

| | | |
|---|---|---|
| CN | 101022875 A | 8/2007 |
| DE | 2161702 A1 | 6/1973 |

(Continued)

OTHER PUBLICATIONS

Notice of Rejection with English Translation, JP 2003-587467, Jul. 24, 2007, 3 pgs.

(Continued)

*Primary Examiner* — Laura Bouchelle
(74) *Attorney, Agent, or Firm* — Nields, Lemack & Frame, LLC

(57) ABSTRACT

The present invention relates to a sterile sample collection device for fluids and a method of using the same. It is comprised of a transfer device having a body with a bore formed through at least a portion of its interior. Contained within the bore is a movable plunger. The body has a first and a second end. The first end contains a face designed to be attached to the upstream component. The second end is connected to tube which is then connected to a collection bag. The plunger has corresponding first and second ends. The first end of the plunger when in the closed position is in alignment with the face of the body which combined form a steamable surface and a sterile barrier against the environment to the rest of the interior of the body, the plunger and downstream components.

28 Claims, 24 Drawing Sheets

(56) References Cited

U.S. PATENT DOCUMENTS

| | | |
|---|---|---|
| 1,831,457 A | 10/1926 | Larsen |
| 1,852,445 A | 4/1932 | Calkins et al. |
| 2,012,836 A | 8/1935 | Talbot et al. |
| 2,122,991 A | 7/1938 | Polston |
| 2,240,888 A | 5/1941 | Hageline |
| 2,426,808 A | 12/1943 | Auer |
| 2,712,881 A | 5/1951 | Mathisen |
| 2,642,256 A | 6/1953 | Stehlin |
| 2,736,201 A | 2/1956 | Ohlsen et al. |
| 2,767,587 A | 10/1956 | Perkins |
| 2,776,473 A | 1/1957 | Dailey et al. |
| 2,779,350 A | 1/1957 | Owens |
| 2,844,964 A | 7/1958 | Guibert |
| 2,859,932 A | 11/1958 | Mackal |
| 2,865,394 A | 12/1958 | Presley |
| 2,872,817 A | 2/1959 | Pitts |
| 2,952,269 A | 9/1960 | Stehlin |
| 3,038,485 A | 7/1961 | Hosek |
| 2,994,224 A | 8/1961 | Brown |
| 3,039,482 A | 6/1962 | Goldberg |
| 3,219,047 A | 6/1962 | Kircher, III et al. |
| 3,097,532 A | 7/1963 | Brown et al. |
| 3,390,677 A | 7/1965 | Razimbaud |
| 3,223,100 A | 12/1965 | Koenig et al. |
| 3,244,376 A | 4/1966 | Thompson |
| 3,260,120 A | 7/1966 | Stilwell |
| 3,276,447 A | 10/1966 | Hamilton |
| 3,319,622 A | 5/1967 | Shiner |
| 3,424,181 A | 1/1969 | Morse |
| 3,479,880 A | 11/1969 | Mutter et al. |
| 3,525,350 A | 8/1970 | Hosek |
| 3,621,719 A | 11/1971 | Goodman et al. |
| 3,633,621 A | 1/1972 | Myers |
| 3,638,499 A | 2/1972 | Saint-Andre |
| 3,678,959 A | 7/1972 | Liposky |
| 3,696,932 A | 10/1972 | Rosenberg |
| 3,736,099 A | 5/1973 | Begg et al. |
| 3,747,411 A | 7/1973 | McDermott et al. |
| 3,776,042 A | 12/1973 | Werra et al. |
| 3,779,082 A | 12/1973 | Galloway |
| 3,802,782 A | 4/1974 | Natelson |
| 3,848,581 A | 11/1974 | Cinqualbre et al. |
| 3,858,449 A | 1/1975 | Singer |
| 3,921,456 A | 11/1975 | Newcomb, Jr. et al. |
| 3,985,332 A | 10/1976 | Walker |
| 4,015,631 A | 4/1977 | Hayes |
| 4,018,059 A | 4/1977 | Hatch |
| 4,034,775 A | 7/1977 | Slagel |
| 4,055,179 A | 10/1977 | Manschot et al. |
| 4,061,709 A * | 12/1977 | Miller et al. .................. 264/293 |
| 4,064,003 A | 12/1977 | Newton |
| 4,094,197 A | 6/1978 | Harris, Sr. et al. |
| 4,207,922 A | 6/1980 | Andrieux et al. |
| 4,244,224 A | 1/1981 | Conn |
| 4,294,247 A | 10/1981 | Carter et al. |
| 4,296,759 A | 10/1981 | Joslin et al. |
| 4,325,401 A | 4/1982 | Ukai et al. |
| 4,346,609 A | 8/1982 | Diesel |
| 4,353,386 A | 10/1982 | Slagel |
| 4,378,824 A | 4/1983 | Carder, Sr. |
| 4,423,641 A | 1/1984 | Ottung |
| 4,423,642 A | 1/1984 | Ottung |
| 4,454,772 A | 6/1984 | Brunner et al. |
| 4,458,543 A | 7/1984 | Mieth |
| 4,479,393 A | 10/1984 | Shores |
| 4,525,127 A | 6/1985 | Welker |
| 4,527,436 A | 7/1985 | Jones |
| 4,537,593 A | 8/1985 | Alchas |
| 4,557,151 A | 12/1985 | Welker |
| 4,569,236 A | 2/1986 | Kitchen et al. |
| 4,580,452 A | 4/1986 | Masson |
| 4,584,887 A | 4/1986 | Galen |
| 4,587,856 A | 5/1986 | Otis |
| 4,587,887 A | 5/1986 | Shibayama et al. |
| 4,622,457 A | 11/1986 | Bradley et al. |
| 4,630,847 A | 12/1986 | Blenkush |
| 4,657,027 A | 4/1987 | Paulsen |
| 4,669,312 A | 6/1987 | Maurer |
| 4,669,321 A | 6/1987 | Meyer |
| 4,704,910 A | 11/1987 | Conrad |
| 4,826,055 A | 5/1989 | Stull |
| 4,836,236 A | 6/1989 | Ladisch |
| 4,838,877 A | 6/1989 | Massau |
| 4,861,239 A | 8/1989 | Simmons et al. |
| 4,913,185 A | 4/1990 | Mattei |
| 4,941,517 A | 7/1990 | Galloway |
| 4,942,901 A | 7/1990 | Vescovini |
| 4,944,875 A | 7/1990 | Gaignet |
| 4,997,108 A * | 3/1991 | Hata .............................. 222/105 |
| 5,058,619 A | 10/1991 | Zheng |
| 5,095,765 A | 3/1992 | Filbey et al. |
| 5,117,872 A | 6/1992 | Yie |
| 5,158,558 A | 10/1992 | Melker et al. |
| 5,161,417 A | 11/1992 | Strong et al. |
| 5,177,872 A | 1/1993 | Lewis et al. |
| 5,246,204 A | 9/1993 | Ottung |
| 5,285,999 A | 2/1994 | Scholz |
| 5,296,197 A | 3/1994 | Newberg et al. |
| 5,360,413 A * | 11/1994 | Leason et al. .................. 604/249 |
| 5,375,477 A | 12/1994 | Neill et al. |
| 5,398,557 A | 3/1995 | Shimizu et al. |
| 5,435,339 A | 7/1995 | Hayes |
| 5,452,746 A | 9/1995 | Hoobyar et al. |
| 5,463,908 A | 11/1995 | Rosolia |
| 5,468,388 A | 11/1995 | Goddard et al. |
| 5,474,546 A | 12/1995 | Ambrisco et al. |
| D366,935 S | 2/1996 | Arthun et al. |
| 5,520,218 A | 5/1996 | Hlavinka et al. |
| 5,525,301 A | 6/1996 | Newberg et al. |
| 5,533,983 A | 7/1996 | Haining |
| 5,535,635 A | 7/1996 | Shaw |
| 5,542,305 A | 8/1996 | Hollinger |
| 5,549,568 A | 8/1996 | Shields |
| 5,585,576 A | 12/1996 | Jaeger |
| D381,067 S | 7/1997 | Karmalm |
| 5,730,418 A * | 3/1998 | Feith et al. .................. 251/149.6 |
| 5,747,708 A | 5/1998 | Weiberth |
| 5,755,155 A | 5/1998 | Buesing |
| 5,766,462 A | 6/1998 | Jones |
| 5,786,209 A | 7/1998 | Newberg |
| 5,820,614 A | 10/1998 | Erskine et al. |
| 5,829,425 A | 11/1998 | Woods et al. |
| 5,868,433 A | 2/1999 | Matkovich |
| 5,885,255 A | 3/1999 | Jaeger, Jr. et al. |
| 5,897,526 A | 4/1999 | Vaillancourt |
| 5,911,252 A | 6/1999 | Cassel |
| 5,948,998 A | 9/1999 | Witte et al. |
| 6,009,684 A | 1/2000 | Buesing |
| 6,030,578 A | 2/2000 | McDonald |
| 6,032,543 A | 3/2000 | Arthun et al. |
| 6,068,617 A | 5/2000 | Richmond |
| 6,096,011 A | 8/2000 | Trombley, III et al. |
| 6,133,022 A | 10/2000 | Newberg et al. |
| 6,145,810 A | 11/2000 | Connolly et al. |
| 6,156,025 A | 12/2000 | Niedospial, Jr. et al. |
| 6,162,206 A | 12/2000 | Bindokas et al. |
| 6,170,800 B1 | 1/2001 | Meloul et al. |
| 6,196,522 B1 | 3/2001 | Yuen et al. |
| 6,210,372 B1 * | 4/2001 | Tessmann et al. ............ 604/181 |
| 6,221,041 B1 | 4/2001 | Russo |
| 6,237,639 B1 | 5/2001 | Jougla et al. |
| 6,254,773 B1 | 7/2001 | Biltoft |
| 6,273,869 B1 | 8/2001 | Vaillancourt |
| 6,306,191 B1 | 10/2001 | McInerney et al. |
| 6,314,987 B1 | 11/2001 | Hay |
| 6,345,640 B1 | 2/2002 | Newberg et al. |
| 6,345,645 B1 | 2/2002 | Kenna et al. |
| D454,173 S | 3/2002 | Almasian et al. |
| 6,354,466 B1 | 3/2002 | Karpisek |
| 6,357,306 B1 | 3/2002 | Jaeger |
| 6,360,794 B1 | 3/2002 | Turner |
| 6,386,137 B1 | 5/2002 | Riche |
| 6,390,127 B2 | 5/2002 | Schick |
| 6,477,906 B1 | 11/2002 | Peterson |

(56) References Cited

U.S. PATENT DOCUMENTS

| | | |
|---|---|---|
| 6,516,677 B1 | 2/2003 | Suter |
| 6,558,365 B2 | 5/2003 | Zinger et al. |
| 6,568,844 B1 | 5/2003 | Arthun et al. |
| 6,601,823 B2 | 8/2003 | Newberg |
| 6,623,631 B1 | 9/2003 | Graus et al. |
| 6,648,006 B1 | 11/2003 | Ostergaard |
| 6,672,561 B2 | 1/2004 | Kerg et al. |
| 6,699,229 B2 | 3/2004 | Zinger et al. |
| 6,715,624 B2 | 4/2004 | Brockwell |
| 6,779,575 B1 | 8/2004 | Arthun |
| 6,860,162 B1 | 3/2005 | Jaeger |
| 6,871,669 B2 | 3/2005 | Meyer et al. |
| 6,916,012 B2 | 7/2005 | Newberg |
| 7,195,181 B2 | 3/2007 | Steingass et al. |
| 7,272,981 B2 | 9/2007 | Bigalke |
| 7,273,550 B2 | 9/2007 | Gutman et al. |
| 7,293,475 B2 | 11/2007 | Furey et al. |
| 7,293,477 B2 | 11/2007 | Furey et al. |
| 7,350,535 B2 | 4/2008 | Liepold et al. |
| 7,473,360 B2 | 1/2009 | Hoffman et al. |
| 7,488,446 B2 | 2/2009 | Meyer et al. |
| 7,578,205 B2 | 8/2009 | Belongia |
| 7,578,936 B2 | 8/2009 | Gaignet et al. |
| 7,597,683 B2 | 10/2009 | Myhrberg et al. |
| RE41,169 E | 3/2010 | Arthun |
| 7,753,340 B2 | 7/2010 | Liepold et al. |
| 7,815,362 B2 | 10/2010 | Myhrberg et al. |
| 7,921,740 B2 | 4/2011 | Furey et al. |
| 7,927,316 B2 | 4/2011 | Proulx et al. |
| 7,959,754 B2 | 6/2011 | Arthun |
| 8,029,023 B2 | 10/2011 | Arthun et al. |
| 8,167,480 B2 | 5/2012 | Myhrberg et al. |
| 8,281,961 B2 | 10/2012 | Martin |
| 2002/0129858 A1* | 9/2002 | Meyer et al. ............ 137/625.48 |
| 2003/0188588 A1 | 10/2003 | Jaeger |
| 2005/0016620 A1 | 1/2005 | Proulx et al. |
| 2005/0035597 A1 | 2/2005 | Bamberger et al. |
| 2005/0132821 A1 | 6/2005 | Furey et al. |
| 2005/0150546 A1 | 7/2005 | Liepold et al. |
| 2005/0285066 A1 | 12/2005 | Huang |
| 2006/0081804 A1 | 4/2006 | Cong |
| 2006/0086922 A1 | 4/2006 | Jensen et al. |
| 2006/0091060 A1 | 5/2006 | Gutman et al. |
| 2006/0142730 A1 | 6/2006 | Proulx et al. |
| 2006/0201263 A1 | 9/2006 | Furey et al. |
| 2006/0211995 A1 | 9/2006 | Myhrberg et al. |
| 2006/0272432 A1 | 12/2006 | Belongia |
| 2007/0106264 A1 | 5/2007 | Proulx et al. |
| 2007/0193375 A1 | 8/2007 | Pandori et al. |
| 2007/0253287 A1 | 11/2007 | Myhrberg et al. |
| 2008/0000820 A1 | 1/2008 | Mitchell |
| 2008/0022785 A1 | 1/2008 | Furey et al. |
| 2008/0087860 A1 | 4/2008 | Vaillancourt et al. |
| 2008/0185552 A1 | 8/2008 | Myhrberg et al. |
| 2008/0277878 A1 | 11/2008 | Arthun et al. |
| 2009/0019952 A1 | 1/2009 | Furey et al. |
| 2009/0054758 A1 | 2/2009 | Dunseath |
| 2009/0101575 A1 | 4/2009 | Alburty et al. |
| 2009/0250157 A1 | 10/2009 | Arthun |
| 2010/0123094 A1 | 5/2010 | Zumbrum |
| 2010/0133459 A1 | 6/2010 | Zumbrum |
| 2010/0290311 A1 | 11/2010 | Myhrberg et al. |
| 2010/0326212 A1 | 12/2010 | Furey et al. |
| 2011/0197989 A1 | 8/2011 | Proulx et al. |
| 2011/0253233 A1 | 10/2011 | Hillier et al. |

FOREIGN PATENT DOCUMENTS

| | | |
|---|---|---|
| DE | 3215799 A1 | 11/1983 |
| DE | 3633431 A1 | 4/1988 |
| DE | 3701250 A1 | 7/1988 |
| DE | 8812723 U1 | 12/1988 |
| DE | 10039196 | 2/2002 |
| DE | 603 10 700 | 10/2007 |
| EP | 0103396 A2 | 3/1984 |
| EP | 0107579 A2 | 5/1984 |
| EP | 0154002 B1 | 9/1985 |
| EP | 0508749 A2 | 10/1992 |
| EP | 0510355 A1 | 10/1992 |
| EP | 0576380 A1 | 12/1993 |
| EP | 0 468 957 B1 | 6/1994 |
| EP | 0684050 | 11/1995 |
| EP | 0691492 A1 | 1/1996 |
| EP | 1008359 A1 | 6/2000 |
| EP | 1 231 699 A1 | 8/2002 |
| EP | 1231699 A1 | 8/2002 |
| EP | 1321699 A2 | 6/2003 |
| EP | 1 499 382 | 11/2003 |
| EP | 1548420 | 6/2005 |
| EP | 1370788 B1 | 11/2005 |
| EP | 0858589 B1 | 12/2005 |
| EP | 1 962 076 A2 | 8/2008 |
| GB | 0 943 132 | 11/1963 |
| GB | 1 381 391 | 1/1975 |
| GB | 1 418 046 | 12/1975 |
| GB | 1 463 303 | 2/1977 |
| GB | 1 479 226 | 7/1977 |
| GB | 1 511 240 | 5/1978 |
| GB | 1573482 | 8/1980 |
| GB | 2327369 | 1/1999 |
| GB | 2365511 | 2/2002 |
| JP | 42-15498 U | 9/1967 |
| JP | 44-4942 U | 2/1969 |
| JP | 49-112631 U | 9/1974 |
| JP | 58-131802 | 9/1983 |
| JP | 59-38278 U | 3/1984 |
| JP | 2-052667 A | 2/1990 |
| JP | 2-71728 A | 3/1990 |
| JP | 2-121679 U | 10/1990 |
| JP | 3-141948 A | 6/1991 |
| JP | 02-118276 | 5/1993 |
| JP | 6-10845 A | 2/1994 |
| JP | 6-023045 A | 2/1994 |
| JP | 06-327772 | 11/1994 |
| JP | 07-051371 | 2/1995 |
| JP | 8-502339 A | 3/1996 |
| JP | 08-168535 | 7/1996 |
| JP | 9-154945 A | 6/1997 |
| JP | 9-512892 A | 12/1997 |
| JP | 11-141713 | 5/1999 |
| JP | 11-270705 | 10/1999 |
| JP | 11-514741 A | 12/1999 |
| JP | 2000-055792 | 2/2000 |
| JP | 2001-170188 A | 6/2001 |
| JP | 2001-269401 A | 10/2001 |
| JP | 2002-510996 A | 4/2002 |
| JP | 2004-332797 A | 11/2004 |
| JP | 2005-519825 | 7/2005 |
| JP | 4332106 | 7/2005 |
| JP | 2006-516723 A | 7/2006 |
| JP | 2008-185218 | 8/2008 |
| JP | 2009-2965 | 1/2009 |
| JP | 2009-192540 | 8/2009 |
| SU | 649954 A | 2/1979 |
| WO | 86/02450 A1 | 4/1986 |
| WO | 90/12972 | 11/1990 |
| WO | 91/00215 A1 | 1/1991 |
| WO | WO 94/08173 | 4/1994 |
| WO | 94/19086 A1 | 9/1994 |
| WO | 95/30856 A1 | 11/1995 |
| WO | 96/30076 | 10/1996 |
| WO | 97/16715 | 5/1997 |
| WO | WO 98/45188 | 10/1998 |
| WO | 98/50105 | 11/1998 |
| WO | 99/03568 | 1/1999 |
| WO | 99/06089 A1 | 2/1999 |
| WO | 99/26580 A1 | 6/1999 |
| WO | 00/78472 A1 | 12/2000 |
| WO | 03/090842 A1 | 11/2003 |
| WO | 03/090843 A1 | 11/2003 |
| WO | 2006/022816 A2 | 3/2006 |
| WO | 2006/026253 A2 | 3/2006 |

(56) References Cited

FOREIGN PATENT DOCUMENTS

| WO | 2008/048511 A2 | 4/2008 |
| WO | 2008/136720 A1 | 11/2008 |
| WO | 2013/011231 A1 | 1/2013 |

OTHER PUBLICATIONS

International Search Report for PCT/US03/12927 dated Aug. 6, 2003.
International Preliminary Examination Report for PCT/US03/12927 dated Feb. 11, 2004.
International Search Report for PCT/US03/13073 dated Aug. 6, 2003.
European Search Report EP 1548420 A3 dated Mar. 13, 2006.
International Preliminary Examination Report for PCT/US03/12924 dated Jul. 8, 2004.
International Search Report for PCT/US03/12924 dated Aug. 6, 2003.
Gore's Preliminary Invalidity Contentions to Plaintiff Millipore Corporation, Document No. 21, filed Oct. 29, 2009 in the United States District Court for the District of Massachusetts, Civil Action No. 09-10765 DPN.
Janetchek, R., "Capsule Filters & Disposable Sterile Processing Systems", Pharmaceutical Processing, p. 8 (Jan. 2001).
Charter Medical, Ltd., Bioprocess Products, "New Quality of Data for Bioprocessings Bags", Pharmaceutical Processing, p. 8 (Jan. 2002).
Greene, R., et al., "Disposable Equipment: A Mainstay in Bioprocessing", Chemical Engineering Progress, pp. 10-11 (Nov. 2002).
Wendt, D., "Disposable processing systems: how suppliers are meeting today's biotech challenges from fluid handling to filtration", Biopharm International, p. 18 (Jul. 2003).
Haughney, H., et al., "Taking Disposable Processing to the Next Level", Biopharm Trends, pp. 20-22 (Jun. 2004).
Tingley, S., "Plastic factory: Disposable biopharmaceutical manufacturing takes a giant leap forward", Alternative Manufacturing, pp. S4-S9 (Feb. 2003).
Tingley, S., "Plastic factory, Part II: The final pieces of the disposable puzzle", Alternative Manufacturing, pp. 12-14 (Jun. 2003).
Millipore's Initial Infringement Contentions, Document No. 19, filed Oct. 8, 2009 in the United States District Court for the District of Massachusetts, Civil Action No. 09-10765 DPW.
Gore's Preliminary Non-Infringement contentions to Plaintiff Millipore Corporation, Document No. 20, filed Oct. 29, 2009 in the United States District Court for the District of Massachusetts, Civil Action No. 09-10765 DPW.
Lynx ST Connectors http://www.millipore.com/catalogue/module/c9131 dated Oct. 30, 2009.
Pure-Flo Hygienic diaphragm valves, actuators, and switch packages, http://www.ittpureflo.com/valvetype.html dated Oct. 30, 2009.
About Fluid Line Technology, http://www.fluidlinetech.com/aboutus.html dated Oct. 30, 2009.
Valves, Gemu Valves and Distributor, Diaphragm Valves, Sanitary Valves, Aseptic Valves, Valves and Fittings, http://www.casellasales.com, dated Oct. 30, 2009.
Allegro Single-use Systems—Recommended Capsule Filters and Membranes, http://www.pall.com/variants/print/biopharm_48022.asp dated Oct. 30, 2009.
Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009.
NovAseptic—How to Use NA sampling system, http://www.novaseptic.se/main.as?typ=6 dated Feb. 13, 2002.
Steam-In-Place Bag Connector, http://www.fluidcomponents.net/tc_tech.html, download on Feb. 18, 2010.
Pharmenta AptiPort Sampling Valve, http://www.web.archive.org/web/20031029084907/http://www.pharmenta.com/aptiport.htm, dated Feb. 18, 2010.
Aranha H. et al., "Disposable processing gains you a competitive edge: enhancing manufacturing capacity with disposable filters, connectors, and membrane chromatography", Biopharm International, p. 50 (Oct. 2003).
Landon, R., et al., "Process PharmaTEC International", issue Jun. 2004 (RP1007EN00), pp. 16-17 (Nov. 2004).
Daily Business Briefing—"Entegris Introduces the First All Teflon PFA" dated Apr. 16, 2002.
Block, S.S. "Disinfection, Sterilization, and Preservation (Fourth Edition)", Lea & Febiger, ISBN:0-8121-1364-0 (1991).
Opticap Valve; Millipore Application Note, Jul. 2000, Gamma Compatible Sterilizing Grade Filter Capsules for Use with Disposable Manufacturing Container; 6-Pages.
Opticap Vent; Millipore Data Sheet, Apr. 2005, "Gamma Compatible Sterilizing-grade Durapore 0.1 um and 0.22 um Filters"; 8-Pages.
Opticap3; Millipore, Nov. 2001, OpticapTM Capsules with Millistake+TM Media User Guide, 4-Pages.
NovaSeptum, NovAseptic, Feb. 2003, "NovaSeptum Liquid Sampling System", 4-Pages.
Microbiological Analysis, Sampling Ports, 1989, p. 130.
Lnyx Trademark to 2,831,931; Apr. 1, 2003.
Office Action dated Aug. 12, 2010 in corresponding U.S. Appl. No. 10/500,077.
Office Actions dated Sep. 22, 2005, Apr. 21, 2006, Nov. 16, 2006, Sep. 10, 2007, Apr. 15, 2008, Nov. 28, 2008, Apr. 14, 2009: Notice of Allowances dated Jan. 25, 2010, Apr. 15, 2010 and Aug. 12, 2010 in corresponding U.S. Appl. No. 10/500,077.
Office Action dated Mar. 19, 2010 in co-pending U.S. Appl. No. 12/284,666.
Office Action dated Mar. 16, 2010 in corresponding U.S. Appl. No. 11/584,301.
Office Actions dated Jan. 30, 2009, Jun. 26, 2009, Aug. 12, 2009, Sep. 25, 2009 and Apr. 6, 2010 in co-pending U.S. Appl. No. 11/878,126.
Memorandum and Order, Document No. 70, dated Sep. 20, 2010, in the United States District Court for the District of Massachusetts, Civil Action No. 09-10765-DPW.
Japanese communication dated Jul. 27, 2010 in corresponding foreign application (JP2008-070904).
Office Action dated Oct. 7, 2010 in corresponding U.S. Appl. No. 11/584,301.
Notice of Allowance and Supplemental Notice of Allowances dated Oct. 1, 2010, Oct. 7, 2010, Oct. 15, 2010 and Oct. 20, 2010 in co-pending U.S. Appl. No. 12/284,666.
European communication dated Oct. 29, 2010 in a corresponding foreign application (EP10179151.5).
European communication dated Oct. 29, 2010 in a corresponding foreign application (EP10179183.8).
Indian communication dated Oct. 18, 2010 in a corresponding foreign application (IN1444/DELNP/2004).
Notice of Allowance dated Dec. 7, 2010 in corresponding U.S. Appl. No. 10/500,077.
Japanese communication dated Dec. 1, 2010 in co-pending foreign application.
Japanese communication dated Dec. 1, 2010 in a co-pending foreign application.
Notice of Allowance dated Feb. 16, 2011 in co-pending U.S. Appl. No. 11/878,126.
Gore's Third Supplemental Response to Millipore's First Set of Interrogatories [Interrogatory No. 11] part 1—pp. 1-43; part 2—pp. 44-85 with Exhibits A-E (334 pages), Exhibits F-G (115 pages) and Exhibits H-I (114 pages), Dec. 21, 2011.
Process Worldwide-PharmaTEC dated Jun. 2004, "Bridging the gap; A case study in the validation of hybrid connectors", 3-pages.
Gore's First Supplemental Response to Millipore's First Set of Interrogatories [Interrogatory Nos. 11, 15 and 16] dated Nov. 1, 2011, 86-Pages.
File history of Trademark U.S. Appl. No. 78/140,217, filed Jul. 1, 2002, 53-Pages.
Office Action dated Apr. 6, 2010 in corresponding U.S. Appl. No. 11/878,126.
Millipore Publication, NovAseptic, NovaSeptum Liquid Sampling system, dated Nov. 2001, P75185, Rev. B (Bates stamp—WLG-DEL00040809-WLG-DEL00040813), 6 pages.

(56) References Cited

OTHER PUBLICATIONS

Pure-Flo: Sample and Bleed Valves for the pharmaceutical and bioprocessing industries, dated Sep. 1992 (Bates stamp WLG=DEL00039389-WLG-DEL00039394), 6-Pages.
Sani-Tech Globe & Angle Valve product information, dated Aug. 1989 (Bates stamp WLG-DEL00040302-WLG-DEL00040304), 3 pages.
Waukesha Cherry-Burrell Manual Valves, dated May 2000 (Bates stamp CSMI000044-CSMI000066), 23-pages.
ESP Sanitary Sample Valves Operation and Maintenance Instructions dated Nov. 1995 (WLG-DEL00039664-WLG-DEL00039678), 16-pages.
Correspondence from T. Pender to C. Burrell dated Dec. 2, 2011 regarding C.A. No. 11-CV-346-SLR (Bates Stamp GF000001-GF000008), 8 pages.
Documents Produced by Third Party Casella Sales and Marketing Inc., related to *W. L. Gore v. Millipore Subpoena*, Nov. 2011, Bates No. CSMI000001 through CSMI000066, 65 pages.
Office Action mailed Nov. 30, 2012 in co-pending U.S. Appl. No. 12/284,666.
Office Action mailed Dec. 21, 2012 in co-pending U.S. Appl. No. 12/638,283.
Japanese Communication, with English translation, mailed Feb. 5, 2013 in corresponding Japanese Patent Application No. JP 2011-179614.
Japanese Communication, with English translation, mailed Mar. 26, 2013 in co-pending Japanese Patent Application No. 2008-288424.
Notice of Allowance mailed Mar. 22, 2013 in corresponding U.S. Appl. No. 13/092,566.
Notice of Allowance mailed Apr. 8, 2013 in co-pending U.S. Appl. No. 12/902,430.
Notice of Allowance mailed Apr. 22, 2013 in corresponding U.S. Appl. No. 11/584,301.
Office Action mailed May 3, 2013 in co-pending U.S. Appl. No. 12/872,436.
Notice of Allowance mailed Jun. 3, 2013 in co-pending U.S. Appl. No. 12/638,283.
Memorandum and Order Denying Millipore's Motion to Alter Judgment and for Reconsideration, U S District Court for the District of Massachusetts, *EMD Millipore Corporation v. W. L. Gore & Associates, Inc.*, Civil Action No. 09-10765-DPW, Document 83, Dated Mar. 20, 2012, 16 pages.
Gore's Prior Art Statement with Exhibits A through I (entire document), U S District Court for the District of Delaware, *W. L Gore & Associates, Inc. v. EMD Millipore Corporation*, Civil Action No. 11-346-SLR, Dated Dec. 21, 2011, 55 pages.
Millipore's List of Claim Terms to Be Construed and Proposed Constructions, U S District Court for the District of Delaware, *W. L. Gore & Associates, Inc. v. EMD Millipore Corporation*, Civil Action No. 11-346-SLR, Dated May 30, 2012, 8 pages.
Gore's List of Claim Terms and Proposed Constructions, U S District Court for the District of Delaware, *W. L. Gore & Associates, Inc. v. EMD Millipore Corporation*, Civil Action No. 11-346-SLR, Dated May 30, 2012, 4 pages.
Millipore's Responsive Constructions of Claim Terms, U S District Court for the District of Delaware, *W. L. Gore & Associates, Inc. v. EMD Millipore Corporation*, Civil Action No. 11-346-SLR, Dated Jun. 20, 2012, 5 pages.
Gore's List of Responsive Claim Constructions, U S District Court for the District of Delaware, *W. L. Gore & Associates, Inc. v. EMD Millipore Corporation*, Civil Action No. 11-346-SLR, Dated Jun. 27, 2012, 8 pages.
Gore's Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 71, Dated Aug. 8, 2012, 3 pages.
Exhibits 1 and 2 to Gore's Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 75, Redacted-Public Version, Dated Aug. 15, 2012, 241 pages.
Plaintiff Gore's Brief in Support of Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 76, Dated Aug. 15, 2012, Redacted—Public Version, 23 pages.
AESSEAL Environmental Technology P04U and PO5U Single Bellows Component Seal Range, Jan. 2006, (Exhibit 4 to the Affidavit of Alexander H. Slocum, Ph.D., US District Court for the District of Massachusetts, *EMD Millipore Corporation v. AllPure Technologies, Inc.*, Civil Action No. 1:11-cv-10221-DPW,Document 66-4, dated May 2, 2012), 5 pages.
Purdue University—School of Mechanical Engineering—International Compressor Engineering Conference, article by J. W. Abar, "End Face Seals for Air-Conditioning Compressors", 1972 (Exhibit 5 to the Affidaivit of Alexander H. Solcum, Ph.D, US District Court for the District of Massachusetts, *EMD Millipore Corporation v. AllPure Technologies, Inc.*, Civil Action No. 1:11-cv-10221-DPW,Document 66-5, dated May 2, 2012), 15 pages.
Memorandum and Order regarding Claim Construction, U S District Court for the District of Massachusetts, *EMD Millipore Corporation v. Allpure Technologies, Inc.*, Civil Action No. 11-10221-DPW, Document 81, Dated Oct. 11, 2012, 34 pages.
Photographs (7 photos) of the Millipore commercially needleless sampling device; available at least as of Feb. 14, 2012, 7 pages.
Photographs (3 photos) of the Millipore Opticap XLT base, commercially available in 2002, no earlier than Jan. 1, 2002, 3 pages.
Photographs (3 photos) of the Millipore Opticap XL 300, commercially available in 2002, no earlier than Jan. 1, 2002, 3 pages.
Brief for Plaintiff-Appellant, US Court of Appeals, Appeal Nos. 2011-1029, 2012-1371, *EMD Millipore Corporation v. W. L. Gore & Associates, Inc.*, Document 40, dated Jul. 25, 2012 and filed Jul. 27, 2012 , 147 pages, submitted in 2 parts.
Brief of Defendant—Appellee W. L. Gore & Associates, Inc., US Court of Appeals, Appeal Nos. 2011-1029, 2012-1371, *EMD Millipore Corporation v. W. L. Gore & Associates, Inc.*, Document 52, filed Oct. 9, 2012, 75 pages.
Reply Brief for Plaintiff-Appellant, US Court of Appeals, Appeal Nos. 2011-1029, 2012-1371, *EMD Millipore Corporation v. W. L. Gore & Associates, Inc.*, Document 57, Dated Nov. 9, 2012, 42 pages.
AllPure Takeone Aseptic Sampling System Overview, 2 pgs. (Deposition Exhibit dated Nov. 12, 2012).
ASI Life Sciences, three 60, Single Use Aseptic Sampling System, www.asisus.com, Jan. 10, 2013, 8 pages.
Fluid Line Technology Corporation, Product Catalog, 32 pages, Bates No. FLT000003-FLT000034, on information and belief available as of about Nov. 2009.
Gore Single-Use Valve, for Steam-In-Place Applications, 4 pgs. 2009.
Gore STA-PURE Fluid Sampling System, for Single-Use Aseptic Applications, Secure Sampling for Bioprocessing Fluids, Dec. 2008, 4 pages.
Lynx ST Connectors, Millipore Data Sheet, Lit. No. 051750EN00, Rev. E, May 2008, 4 pages.
International Application No. PCT/US03/13073, filed Apr. 25, 2003, and Request for Express Abandonment of U.S. Appl. No. 10/423,131, filed Sep. 11, 2003, 56 pages.
MicropreSure Sanitary Sampling Valves, Millipore Data Sheet, Lit. No. DS1006EN00, May 2005, 4 pages.
Millipore Express SHF Hydrophilic Cartridge Filters, Data Sheet, May 16, 2013, www.millipore.com/catalogue, 2 pages.
Millipore, Hydrophilic Durapore Cartridges and Capsules User Guide, Lit. No. RF 1510EN00, Jan. 2002, 56 pages.
Millipore, Milliflex-P Sanitary Sampling Valves, Operation and Maintenance Instructions, Jul. 2006, 17 pages.
NovaSeptum sampling systems, EMD Millipore Data Sheet, Jun. 2012, Lit. # DS0050EN00, Rev. E., 10 pgs.
NovaSeptum sampling systems, Merck Millipore Data Sheet, Apr. 2013, Lit. # DS0050EN00, Rev. H., 10 pgs.
Millipore, NovaSeptum AV Sterile Sampling System, for liquid sampling, User Guide, Lit. No. 00000069TP, Rev. A., Jun. 2006, 2 pages.

(56) References Cited

OTHER PUBLICATIONS

Millipore Opticap XL and XLT Disposable Capsules, Millipore Corporation, Lit. No. PB1700EN00, Rev. B, Jun. 2004, 4 pages.
Pharmaceutical Engineering, vol. 23, No. 3, May/Jun. 2002, pp. 1-8, "Single-Use Disposable Filling for Sterile Pharmaceuticals", Belongia, et al.
Redacted email, dated Jun. 4, 2012, regarding Disposable Steam Connector, 2 pages.
Millipore Application Note, Lit. No. AN7428EN00, Rev. A, "Risk Free Connection of Sterilized Single-Use Fluid Path Assemblies to Stainless Steel SIP Systems with Lynx ST (Steam-To) Connectors", May 2008, 8 pages.
Millipore, Series 2000, Single Sanitary Cartridge Housing, Instructions for Installation and Maintenance, Lit. No. P35265, Rev. A, Feb. 2000, 12 pages.
ThermoScientific, Data Sheet 053, Rev. 2, "Aseptic Connection Devices", 2008, 2 pages.
Final Rejection mailed Jun. 19, 2013 in co-pending U.S. Appl. No. 12/291,814.
Notice of Allowance mailed Mar. 29, 2012 in co-pending U.S. Appl. No. 12/284,666.
English translation of Chinese Communication issued Aug. 29, 2012 in co-pending Chinese patent application No. CN 201010531386.0.
Japanese Communication, with English translation, dispateched Aug. 21, 2012 in co-pending Japanese patent application No. JP 2010-245357.
Office Action mailed Aug. 29, 2012 in co-pending U.S. Appl. No. 12/902,430.
Office Action mailed Oct. 3, 2012 in corresponding U.S. Appl. No. 13/092,566.
Final Rejection mailed Oct. 10, 2012 in co-pending U.S. Appl. No. 12/872,436.
Office Action mailed Oct. 5, 2012 in co-pending U.S. Appl. No. 12/291,814.
Notice of Allowance mailed Jul. 3, 2013 in corresponding U.S. Appl. No. 13/092,566.
Notice of Allowance mailed Jul. 5, 2013 in corresponding U.S. Appl. No. 11/584,301.
Notice of Allowance mailed Jun. 21, 2013 in co-pending U.S. Appl. No. 12/284,666.
Notice of Allowance mailed Jul. 8, 2013 in co-pending U.S. Appl. No. 12/284,666.
ITT Dualrange Control Valve. Data Sheet [online], Pure-Flo. Retrieved from the Internet: www. ittpureflo.com (2 pages), document created Jan. 12, 2007 according to document properties.
Sanitary Inline Bleed and Sample Valves. Datasheet [online], Fluid Line Technology, Retrieved from the Internet: www.fluidlinetech.com (1 page), document created on Mar. 2, 2009 according to document properties.
"Sip-Able Sample Valve," Datasheet [online]. Retrieved from the Internet: www.fluidlinetech.com (1 page), product offered online as early as Jun. 26, 2007, according to URL search performed on http://web.archive.org.
Entegris Impact Asymmetric Disposable Filters, Product Information brochure, 4414-5723ENT-0511, 2006, 6 pages.
Entegris Impact Mini Disposable Filters, Product Information brochure, 4414-2646ENT-1006, 2006, 4 pages.
Millipore Corporation, Milli-Q Direct Water Purification System brochure, Lit. No. PB1032EN00, Jan. 2012, 8 pages.
Millipore Corporation, Milli-Q Advantage A10 Water Purification Systems brochure, Lit. No. PB0001EN00, 2013, 12 pages.
Fluid Line Technology Corporation Documents produced in *Gore* v. *Millipore*, Nov. 28, 2011, Bates # FLT000001 through Bates # FLT000103, 48 pages.
Allegheny Bradford Corporation's Objections and Responses to Subpoena, Civil Action No. 1:11-cv-00346-SLR, dated Dec. 15, 2011 in the USDC for the District of Delaware, and Bates # ABC00001 through Bates # ABC00012, 19 pages.
Gore's Fourth Supplemental Response to Millipore's First Set of Interrogatories [Interrogatories Nos. 11 and 12], Civil Action No. 11-346-SLR in the USDC for the District of Delaware, dated May 9, 2012, 172 pages.
ITT Dualrange Control Valve. Data Sheet [online], Pure-Flo. Retrieved from the Internet: www. Lttpureflo.com (2 pages). [no date].
Sanitary Inline Bleed and Sample Valves. Datasheet [online], Fluid Line Technology, Retrieved from the Internet: www.fluidlinetech.com (1 page). [no date].
Pure-Flo Solutions, Pure-Flo Radial Seated Tank Bottom Diaphragm Valve, Datasheet [online], ITT Industries, 2001. (2 pages).
Casella Sales & Marketing Inc., CSMI Sample Valves. Datasheet [online], 2007, Retrieved from the Internet: www.casellasales.com (2 pages).
"New quality of data for bioprocessing bags. (Application Area)." Pharmaceutical Processing, Jan. 2002, Charter Medical, Ltd., Bioprocess Products, Retrieved from the Internet: <URL: http://www.accessmylibrary.com/coms2/summary_0286-25022745_ITM>, pp. 1-2.
"Rapid Aseptic Fluid Transfer System Introduction", Stedim Blosystems. [online]. Retrieved from the Internet: <URL: http: www.stedim.com/p2A_IDS_introduction.php> (2 pages), dated Nov. 21, 2007.
"Sip-Able Sample Valve," Datasheet [online]. Retrieved from the Internet: www.fluidlinetech.com (1 page). [no date].
Preliminary Noninfringement and Invalidity Disclosures of Allpure Technologies, Inc., Document 22, filed Jul. 20, 2011 in the United States District Court for the District of Massachusetts, Civil Action No. 11-cv-10221-DPW. (15 pages).
Office Action mailed Jun. 26, 2012 in co-pending U.S. Appl. No. 12/872,436.
Office Action mailed Dec. 8, 2011 in co-pending U.S. Appl. No. 12/291,814.
Final Rejection mailed Jun. 20, 2012 in co-pending U.S. Appl. No. 12/291,814.
Notice of Allowance mailed Jul. 16, 2013 in co-pending U.S. Appl. No. 12/902,430.
Notice of Allowance mailed Jul. 18, 2013 in co-pending U.S. Appl. No. 12/638,283.
Office Action dated Mar. 16, 2010 in a co-pending (U.S. Appl. No. 11/584,301).

\* cited by examiner

DISPOSABLE, STERILE FLUID TRANSFER DEVICE

CROSS-REFERENCE TO RELATED APPLICATIONS

This application is a division of co-pending U.S. application Ser. No. 10/500,077, filed Jun. 23, 2004, which is a U.S. National Stage Application of International Application No. PCT/US03/12927, filed on Apr. 25, 2003, which claims the benefit of U.S. Application No. 60/375,747, filed on Apr. 26, 2002. The entire contents are incorporated in their entirety herewith.

The present invention relates to a disposable, sterile fluid transfer device. More particularly, it relates to a disposable sterile fluid transfer device, preferably in the form of a connector or valve for use in the pharmaceutical and biopharmaceutical industry.

BACKGROUND OF THE INVENTION

In the pharmaceutical, biotechnology and even food, beverage and cosmetics industries, it is often desired to provide a processing system that is capable of handling fluids in a sterile manner. This is designed to prevent unwanted, often dangerous organisms, such as bacteria as well as environmental contaminants, such as dust, dirt and the like from entering into the process stream and/or end product. It would be desirable to have a completely sealed system but this is not always possible with the processes that take place in production.

There is a need for the introduction or removal of materials from the process stream in order to add components of the product, such as media or buffers to a bioreactor; withdraw samples from the process stream to check for microbial contamination, quality control, process control, etc; and to fill the product into its final container such as vials, syringes, sealed boxes, bottles and the like.

Typically, the systems have been made of stainless steel and the system is exposed to live steam before use and then cleaned with chemicals such as caustic solutions after use to ensure that all contaminants are removed.

Steaming is the most effective means of sterilization. The use of steam in a set system is known as steaming in place or SIP. Saturated steam carries 200 times the BTU heat transfer capacity of heated air because of the latent heat released by the steam as it changes from vapor to liquid.

Several disadvantages exist with the use of steam. Any connections to or openings of the system made after the system has been SIP'd is an aseptic (but not sterile) connection or opening. This increases the risk of contamination of the entire system. One typically uses alcohol wipes or an open flame to clean the components to be connected, (e.g. connecting a sample collection bag to a system after SIP has occurred) and thus minimize the risk of contamination.

Also the high temperatures and pressure differentials of the steam make the selection of filter materials and components very difficult and limited and even then an accidental pressure differential at high temperatures can cause a filter, membrane or other non-steel component to fail.

Additionally, such systems that are reused need to undergo rigorous testing and validation to prove to the necessary authorities that the system is sterile before each use. The expense of validation as well as the cleaning regiment required is very high and very time consuming (typically taking 1 to 2 years for approval). In addition, some components are very difficult to adequately clean after use in preparation for their next use. Manufacturers are looking for ways to reduce both their costs and the time to market for their products. One possible approach is to adopt an all disposable system that is set up in a sterile fashion, used and then thrown away.

The present invention provides a connector that can be used in either the traditional steel system or disposable system which provides both a means for steam sterilizing the mating point of the connector to the system as well as providing a sterile downstream area or component, in pre-sterile condition, that can be disposed of after use and not be recleaned.

SUMMARY OF THE INVENTION

The present invention relates to a sterile transfer device for fluids, be they liquids or gases. It is comprised of a body having a bore formed through at least a portion of its interior. Preferably, it is a central bore formed through the entire length of the body. Contained within the bore is a movable plunger. The body has a first and a second end. The first end contains a face designed to be attached to the upstream component. The second end is connected to a downstream component such as a filter, pipeline, sample bag and the like. The plunger has corresponding first and second ends. The first end of the plunger when it the closed position is in alignment with the face of the body which combined form a steamable surface and a sterile barrier against the environment to the rest of the interior of the body, the plunger and downstream components.

The downstream components are assembled to the device and it is placed in the closed position. The entire device and downstream components are sterilized, such as with gamma radiation. In use the device and downstream components are attached by the face to the upstream component such as a filter outlet, a tank outlet, a "T" of a pipe and secured in place. The system and the face of the device are then steam sterilized in place. The device is then selectively opened when needed establishing a sterile pathway through the device to the downstream components.

IN THE DRAWINGS

DETAILED DESCRIPTION OF THE INVENTION

The present invention is a sterile fluid transfer device, preferably in the form of a connector or a valve.

Figure 1:
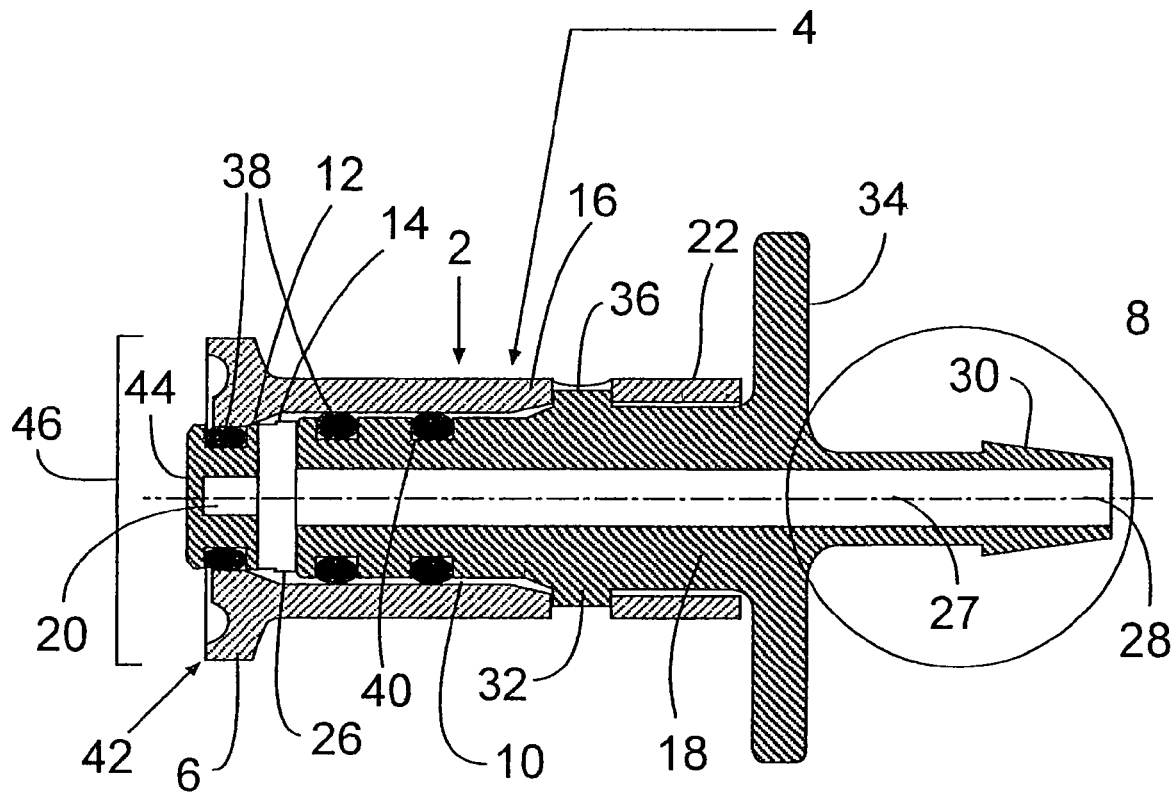
FIG. 1 shows a cross sectional view of a first embodiment of the present invention in a closed position.

A first embodiment of the present invention is shown in FIG. 1. The device 2 is formed of a body 4 having a first end 6 and a second end 8. The body 4 also has a bore 10 extending in this embodiment from the first end 6 to the second end 8. The bore 10 as shown is formed of three sections each with a different diameter. There is the first bore section 12 which has a first set diameter, a transition bore section and a second bore section which has a second set diameter that is greater than the first set diameter of the first bore section 12. The transition bore section 14 is arranged between the first and second bore sections 12, 16 and has an outwardly tapering diameter along its length with the diameter of the transition section 14 adjacent the first bore section 12 being equal to the first set diameter and the diameter of the transition section 14 adjacent the second bore section 16 being equal to the second set diameter. The diameter of the transition section between the first and second bore sections is preferably a linear outward progression between the two bore sections.

Contained within the bore is a plunger 18 which has a shape corresponding to that of the bore 14. The plunger has a first portion 20 having a diameter equal to or less than that of the diameter of the first bore section, a second plunger portion 22 having a diameter equal to or less than that of the second bore section and a transitional portion 24 between the first and second plunger portions 20, 22 having an outwardly tapered diameter between the first and second plunger portions 20, 22 equal to or less than the diameter of the transition bore section 14. The plunger 18 also contains one or more openings 26 in either the transitional portion 24 or the first or second portions 20, 22 as well as a fluid channel 27 that forms a fluid connection to a downstream component or tubing (not shown).

As shown, the farthest part 28 of the second portion 22 contains a barb design 30 to, connect to the next downstream component. The plunger also contains several preferable elements that are useful but not necessary to the invention. Included among these are a cam 32 and a connector handle 34. The cam 32 rides in a cam slot 36 formed in the body 4 and together are used to limit the length of travel of the plunger 18 in the bore 14.

The device is shown in FIG. 1 in the closed position. One or more seals 38 are arranged along the length of the plunger 18 to form a liquid tight seal between various portions of the plunger 18 and the bore 14 when they are in the closed or open positions. As shown the seals 38 are contained in grooves 40.

The device 2 is attached to an upstream component or pipe by a sanitary flange 42 formed as part of the body 4. In the closed position the flange 42 and the farthestmost end of the first portion of the plunger 44 form a face 46 against the rest of the system. The flange 42 can be attached to the upstream component or pipe by a clamp such as a Tri-Clover™ fitting, Ladish™ fitting, ClickClamp™ clamp or the like. This face 46 is capable of withstanding steam treatment when in the device is in the closed position as will be described in more detail below.

Figure 2:
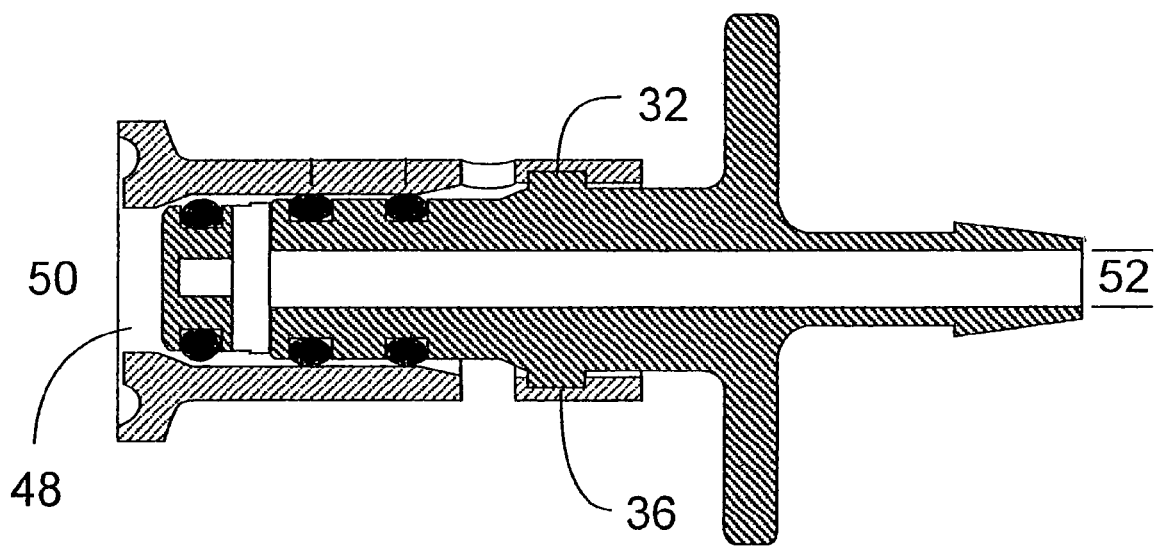
FIG. 2 shows a cross sectional view of the first embodiment of the present invention of FIG. 1 in an open position.

FIG. 2 shows the device 2 of FIG. 1 in the open position. To the extent that the same reference numbers apply to both FIGS. 1 and 2 they have been kept the same.

In FIG. 2, the plunger has been moved from the closed position of FIG. 1 to an open position. The farthestmost end of the first portion of the plunger 44 has been moved back from the face 46 providing a passageway 48 to the bore 14 and the one or more openings 24 and the fluid channel 26 forming a fluid connection between the upstream 50 and downstream sides 52 of the device 2. As shown, the plunger is moved rearward or downstream and rotated at the same time, as evidenced by the movement of the cams 32 in the cam slot 36.

Figure 3:
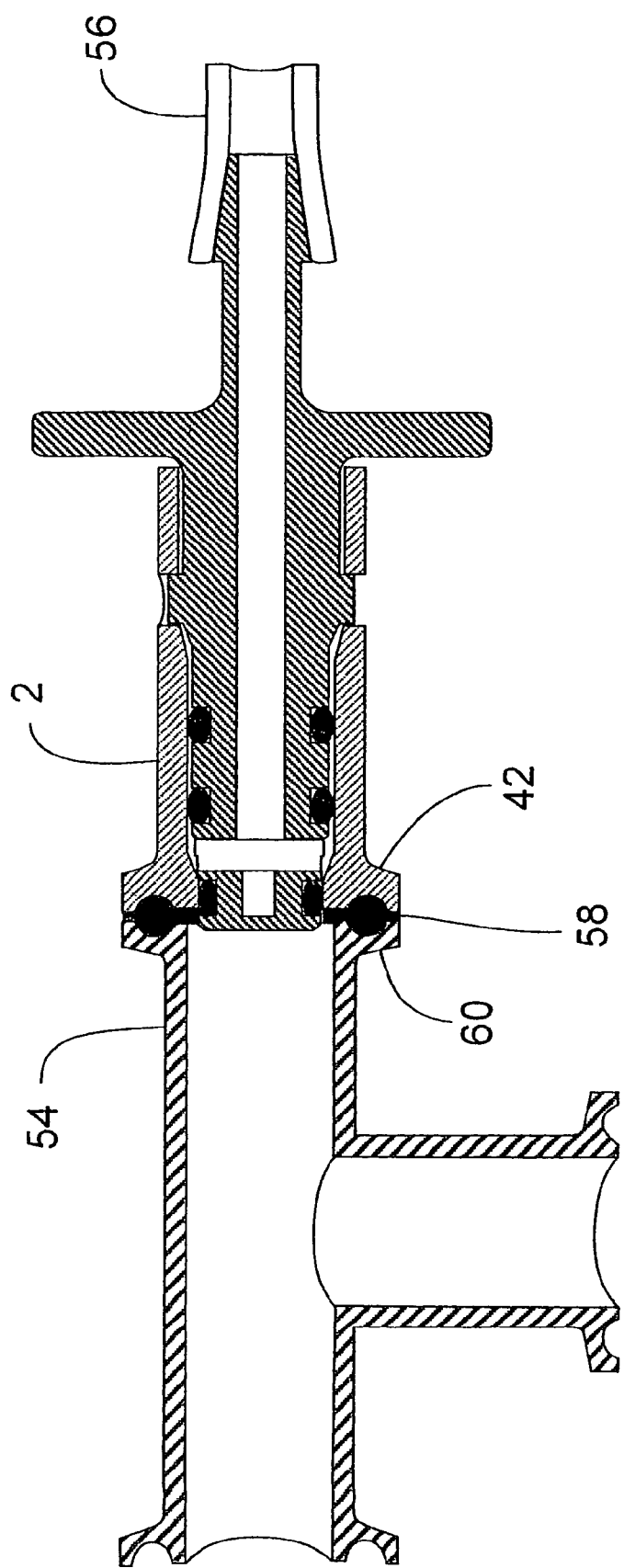
FIG. 3 shows a cross sectional view of the first embodiment of the present invention of FIG. 1 mounted to an upstream component.

FIG. 3 shows the device 2 of FIG. 1 mounted to an upstream component 54, in this instance a "T" pipe and a downstream component 56, in this instance a piece of hose or plastic pipe. Also shown is liquid tight seal 58 formed between the flange of the device 2 and a flange 60 (clamp not shown).

Figure 4:
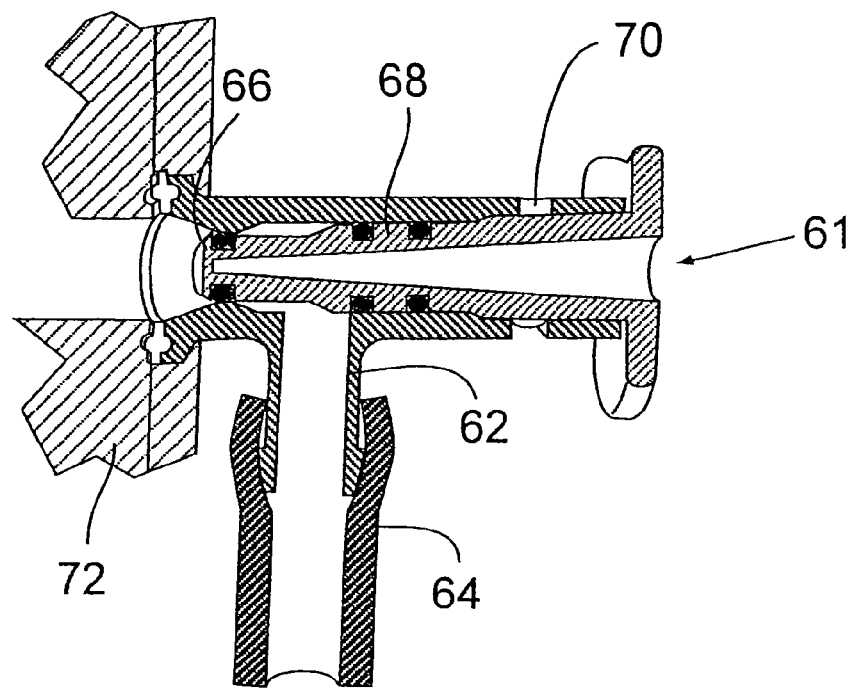
FIG. 4 shows a cross sectional view of a second embodiment of the present invention in a closed position.
Figure 5:
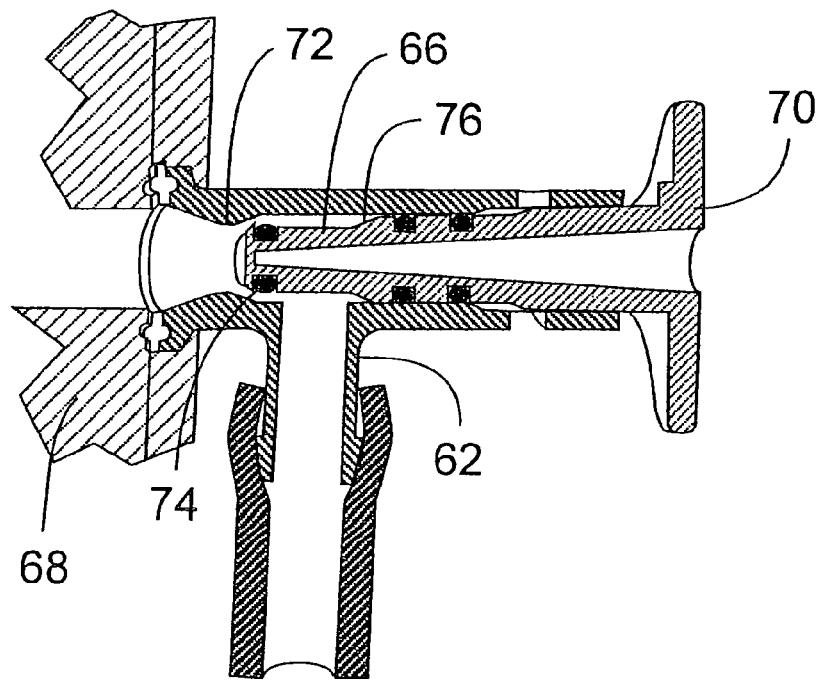
FIG. 5 shows a cross sectional view of a second embodiment of the present invention of FIG. 3 in an open position.

FIGS. 4 and 5 show an embodiment of the present device 61 in which there is no fluid passage formed in the plunger. Instead, the body contains a port 62 which provides the fluid connection to the downstream component 64, in this instance a piece of plastic piping. As shown in the closed position, the farthestmost end 66 of the first portion 68 of the plunger 70 seals off the downstream side of the device 61 from the upstream component 72. The port 62 is shown as being at a 90 degree angle to the length of the body, but it may be any other desired angle.

As shown in FIG. 5, when the device of FIG. 4 is opened, the farthestmost end 66 of the first portion 68 of the plunger 70 has been moved back from the face 72 providing a passageway 74 to the bore 76 and the port 62 so as to provide fluid communication between the upstream component 72 and the downstream component 64 through the device 61.

Figure 6:
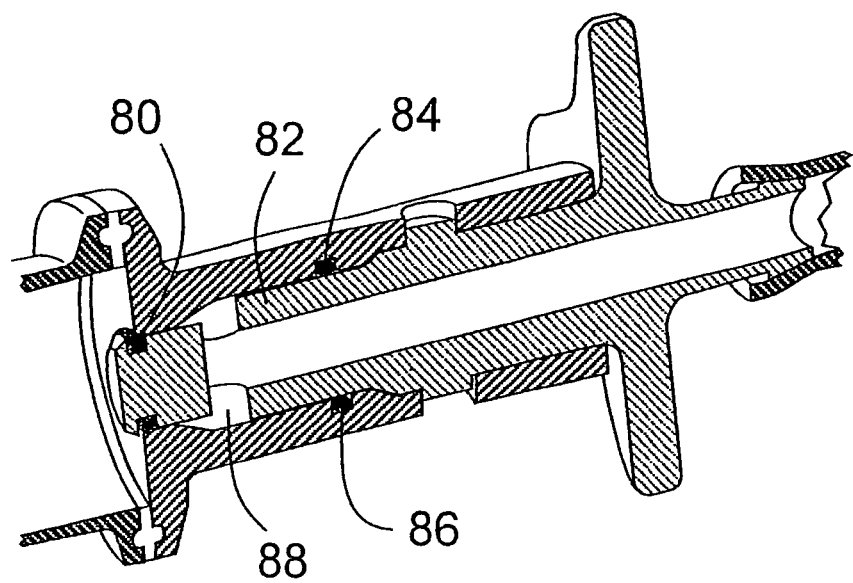
FIG. 6 shows a cross sectional view of another embodiment of the present invention.

As shown in FIGS. 1-5, the seals may be mounted on the plunger of the device. Further, the seals shown in FIGS. 1-5 are O-rings, either pre-formed and retained within grooves on the plunger or formed in place in the grooves of the plunger. However, if desired, different configurations of seals and their placements can be used. For example, FIG. 6 shows some seals 80 formed on the plunger 82 with other seals 84 held in grooves 86 in the inner surface of the bore 88.

Figure 7:
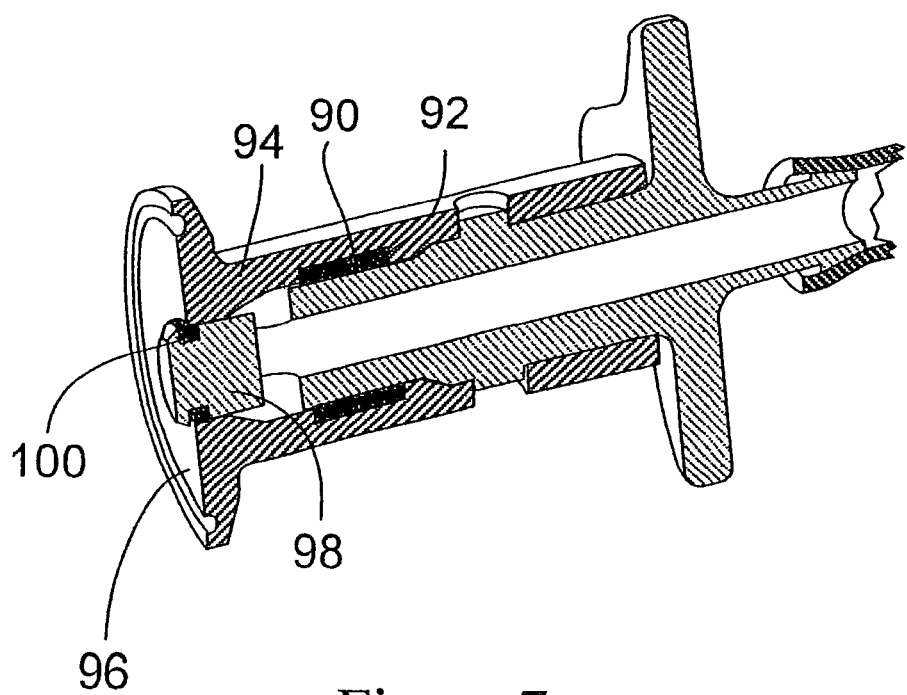
FIG. 7 shows a cross sectional view of another embodiment of the present invention.

FIG. 7 shows an embodiment with a linear or gland seal 90 is retained within a groove 92 on the inner wall of the body 94 and other seals 96 attached to the plunger 98 in grooves 100.

Figure 8:
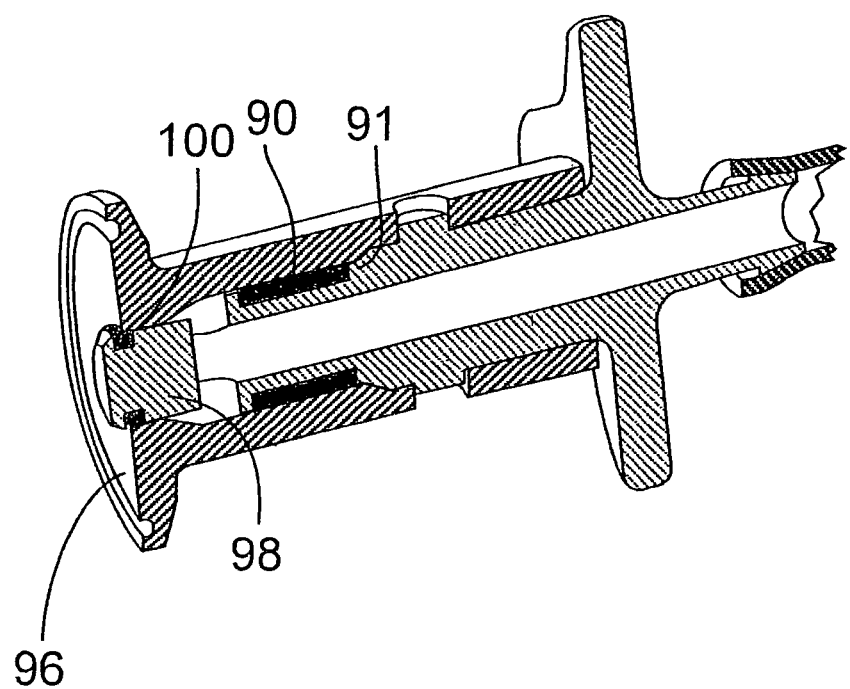
FIG. 8 shows a cross sectional view of another embodiment of the present invention.

FIG. 8 shows a similar design to that of FIG. 7 except that the gland seal 90 is formed on the outer wall 91 of the plunger 98 and other seals 96 are attached to the plunger 98 in grooves 100.

As this is device is provided in a sterile condition, i.e. the interior of the system and any component connected downstream of the device is pre-sterilized such as with gamma radiation, ethylene gas or the like and shipped in a sterile condition, some type of use indicator would be helpful so one knows when a system has been used and should therefore be replaced.

Figure 9A:
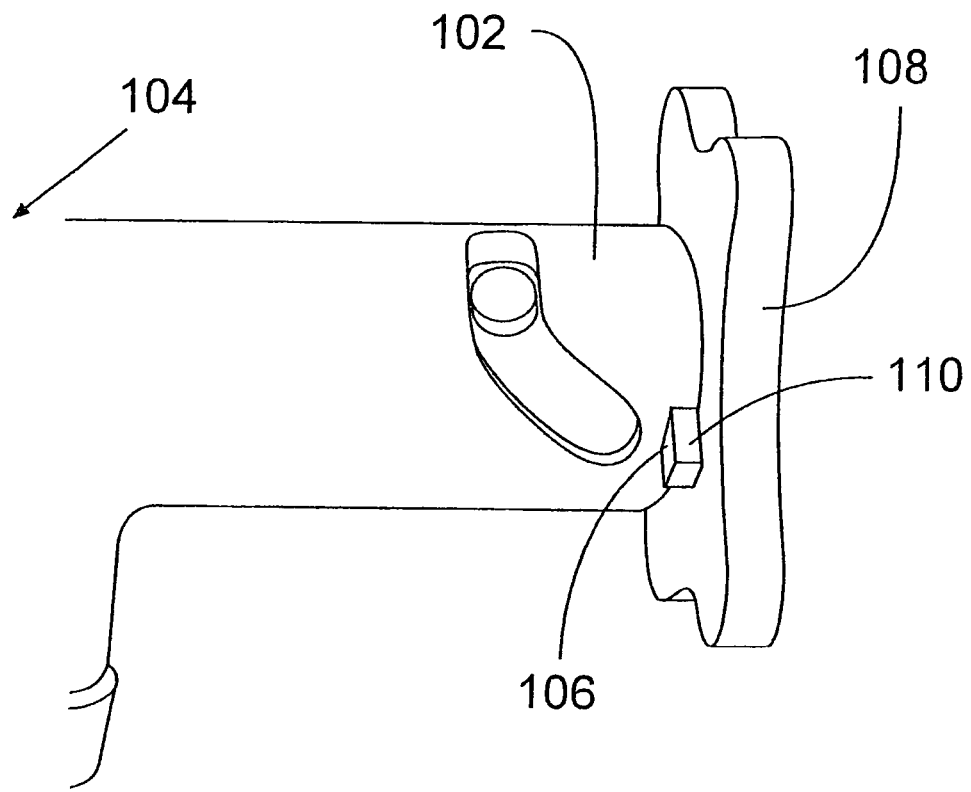
FIG. 9A shows a perspective view of a locking mechanism of the present invention in unopened condition.

FIG. 9A shows a first embodiment of an indicator useful on the present invention. As shown in the FIG. 9A, the body section 102 distal from the steamable face 104 has a series of one or indentations or locking recesses or fixed pawls 106. The plunger 108 has a mating detent 110 which is located in one of the recesses before the device is sterilized. The device is shipped in this sterile condition with the detent remaining in the recess. In fact, the detenurecess combination works to ensure that the device doesn't accidentally open due to vibration or handling during shipping.

Figure 9B:
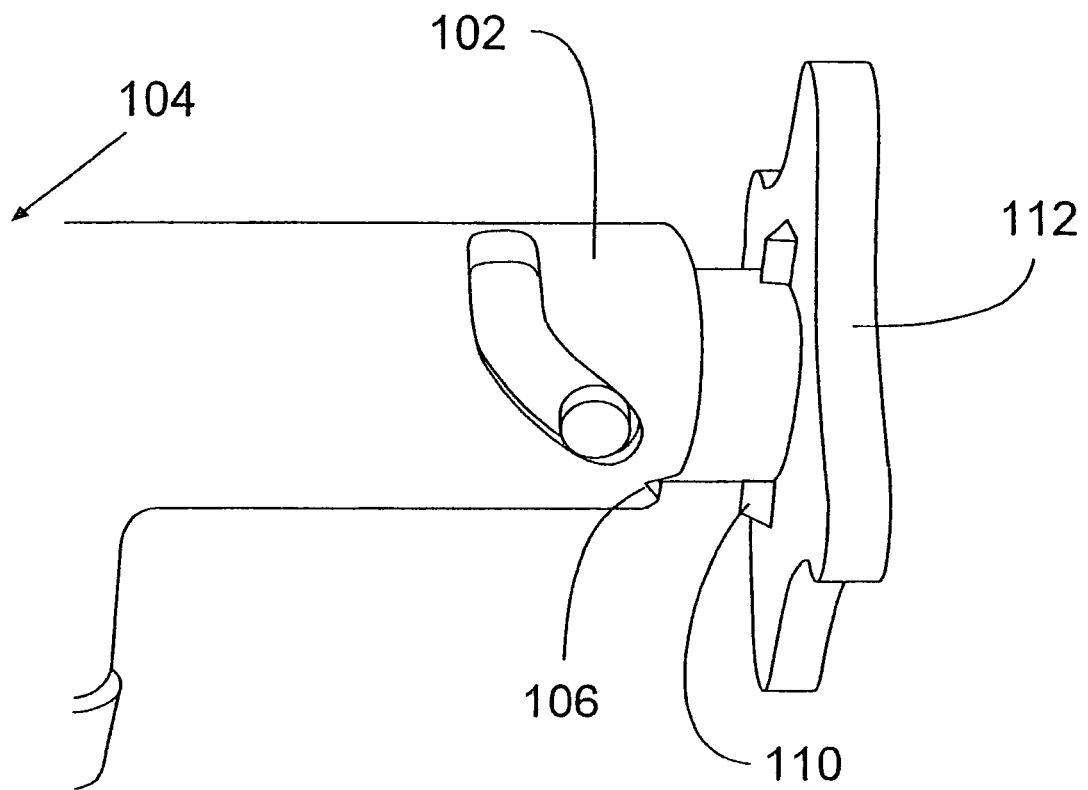
FIG. 9B shows a perspective view of the locking mechanism of 9A of the present invention in the opened condition.

The device is then taken from its sterile container in the closed position of 9A and attached by its face to the system. The face is then steam sterilized. The device is then opened by rotating the handle to an open position as shown in FIG. 9B.

Figure 9C:
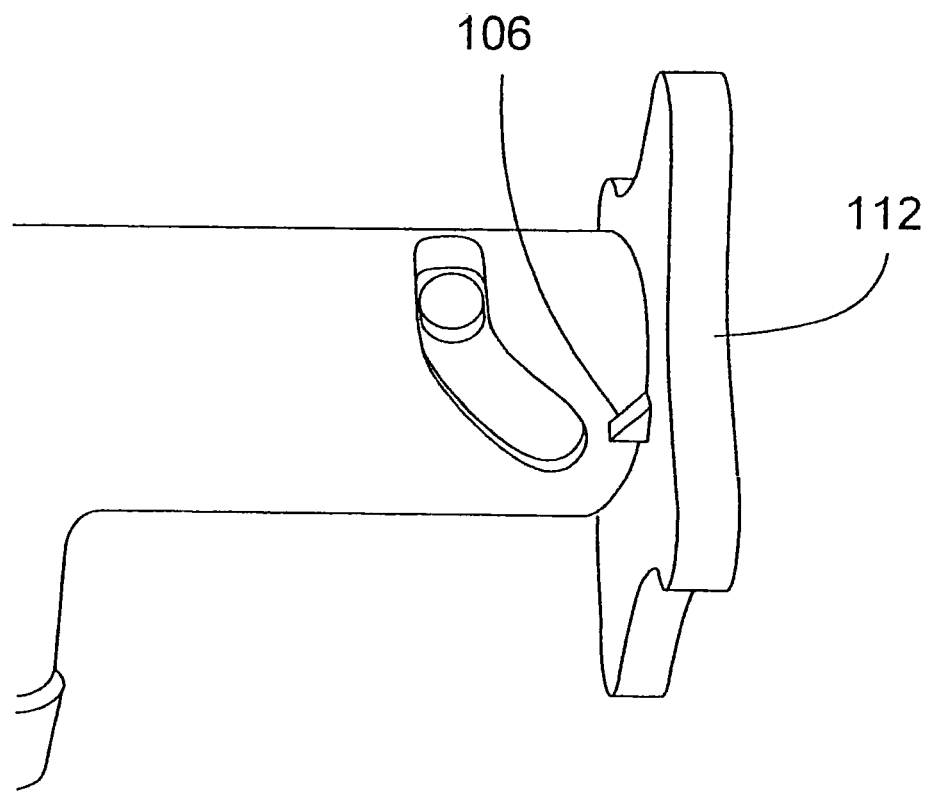
FIG. 9C shows a perspective view of the locking mechanism of 9A of the present invention in the reclosed position.

When the device is closed after use, the handle 112 of the plunger 108 is capable of moving the detent 110 past the first recess and into the second recess 106 as shown in FIG. 9C. This provides a visual indication to the user that the device is no longer sterile. In addition, it provides a manual indication to the user that the device has been used as the detent 110 has to be turned past the two recesses 106, each with an affirmative clicking action before the device can be opened. Moreover, one can design the walls of the farthermost (used condition) recess 106 so that the movement out of the recess requires an extraordinary amount of force to again indicate to the user that the device has been used and shouldn't be reused.

Figure 10A:
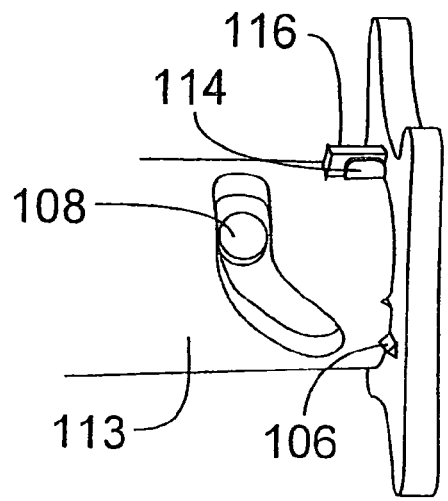
FIG. 10A shows a perspective view of a locking mechanism of the present invention in unopened condition.

FIG. 10A shows another embodiment of an indicator useful on the present invention. As shown in the FIG. 10A, the body section 113 distal from the steamable face (not shown) has a series of one or indentations or locking recesses or fixed pawls 106 as well as one or more breakaway tabs 114. The plunger 108 has a mating detent 110 which is located in one of the recesses 106 before the device is sterilized as well as a breaking bar 116. The device is shipped in this sterile condition with the detent remaining in the recess and the breaking bar being positioned behind the breakaway tab.

Figure 10B:
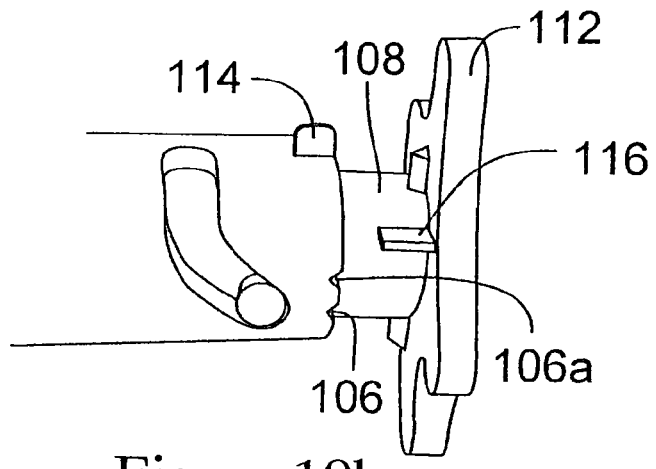
FIG. 10B shows a perspective view of the locking mechanism of 10A of the present invention in the opened condition.

The device is then taken from its sterile container in the closed position of 10A and attached by its face (not shown) to the system. The face is then steam sterilized. The device is then opened by rotating the handle 112 to an open position as shown in FIG. 10B. In doing so the breaking bar 16 rotates past and over the breakaway tab 114, causing it to be bent over or removed altogether.

Figure 10C:
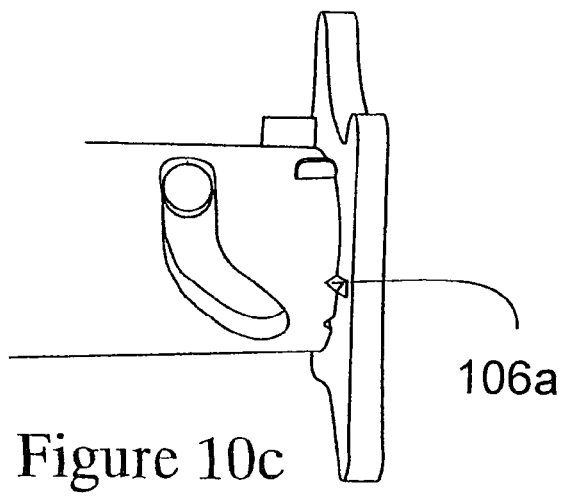
FIG. 10C shows a perspective view of the locking mechanism of 10A of the present invention in the reclosed position.

When the device is closed after use, the handle 112 is capable of moving the detent 110 past the first recess 106 and into the second recess 106A as shown in FIG. 10C.

Figure 11A:
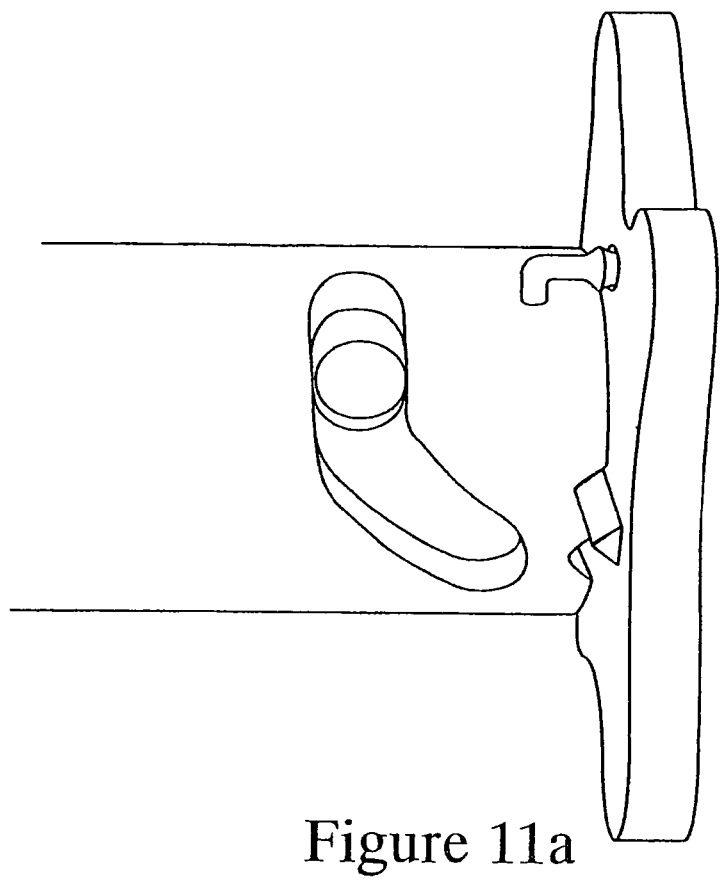
FIG. 11A shows a perspective view of a locking mechanism of the present invention in unopened condition.
Figure 11B:
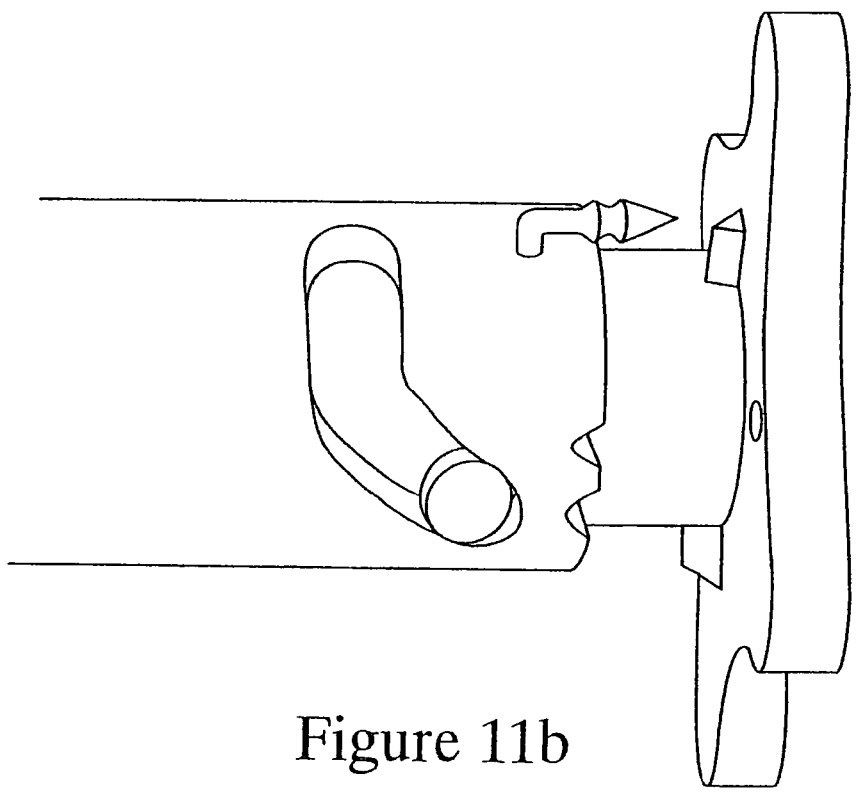
FIG. 11B shows a perspective view of the locking mechanism of 11A of the present invention in the opened condition.

FIGS. 11A and B show a plastic feature extending from the body that forms another breakaway (or bend-away) indicator. FIG. 11A, shows the valve in its shipped (or pre-sterilized) position. It is intended that when the valve is opened, this protruding feature will break away or at least bend away from its original position, thereby indicating that the valve has been actuated and should not be used again once it has been subsequently closed. FIG. 11B shows the valve in the open position, showing the tab feature as being bent.

Figure 12A:
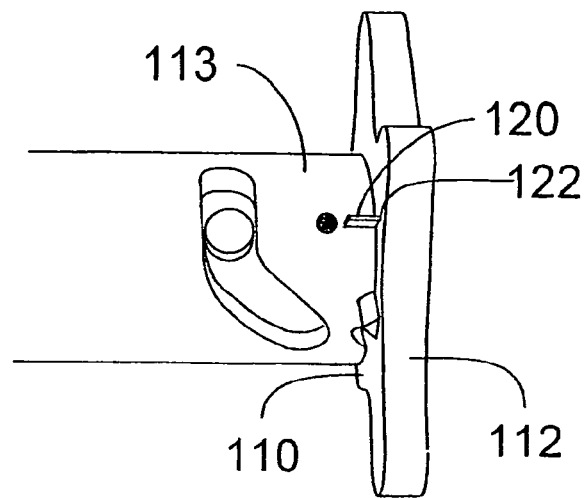
FIG. 12A shows a perspective view of a locking mechanism of the present invention in unopened condition.

FIG. 12A shows another embodiment of an indicator useful on the present invention. As shown in the FIG. 12A, the body section 113 distal from the steamable face (not shown) has a series of one or indentations or locking recesses or fixed pawls 106 as well as one or more tab retainers 120. The plunger 108 has a mating detent 110 which is located in one of the recesses 106 before the device is sterilized as well as a breakaway or fold over tab 122. The device is shipped in this sterile condition with the detent remaining in the recess and the breaking bar being positioned behind the breakaway tab.

Figure 12B:
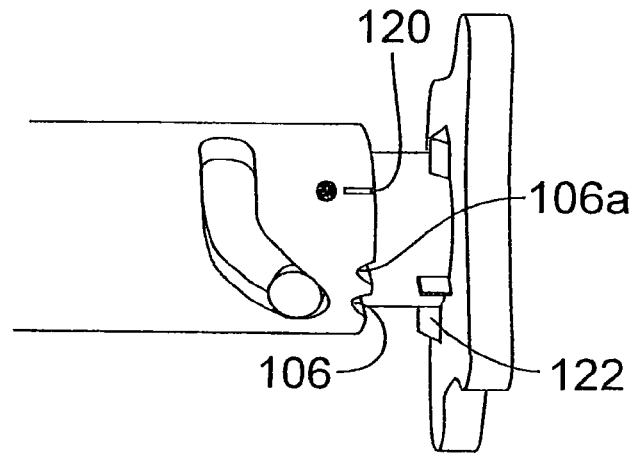
FIG. 12B shows a perspective view of the locking mechanism of 12A of the present invention in the opened condition.

The device is then taken from its sterile container in the closed position of 12A and attached by its face (not shown) to the system. The face is then steam sterilized. The device is then opened by rotating the handle 112 to an open position as shown in FIG. 12B. In doing so the tab 122 in tab retainer 120 rotates out of the retainer 120, causing it to be bent over or removed altogether.

Figure 12C:
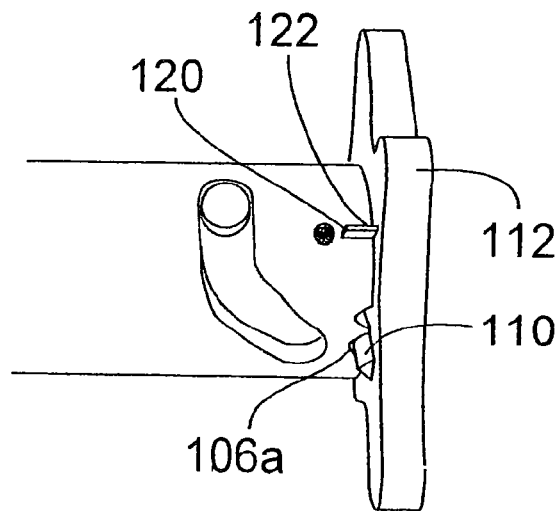
FIG. 12C shows a perspective view of the locking mechanism of 12A of the present invention in the reclosed position.

When the device is closed after use, the handle 112 is capable of moving the detent 110 past the first recess 106 and into the second recess 106A as shown in FIG. 12C with the tab 122 if it remains being bent up and not being returning to the retainer 120.

Figure 13:
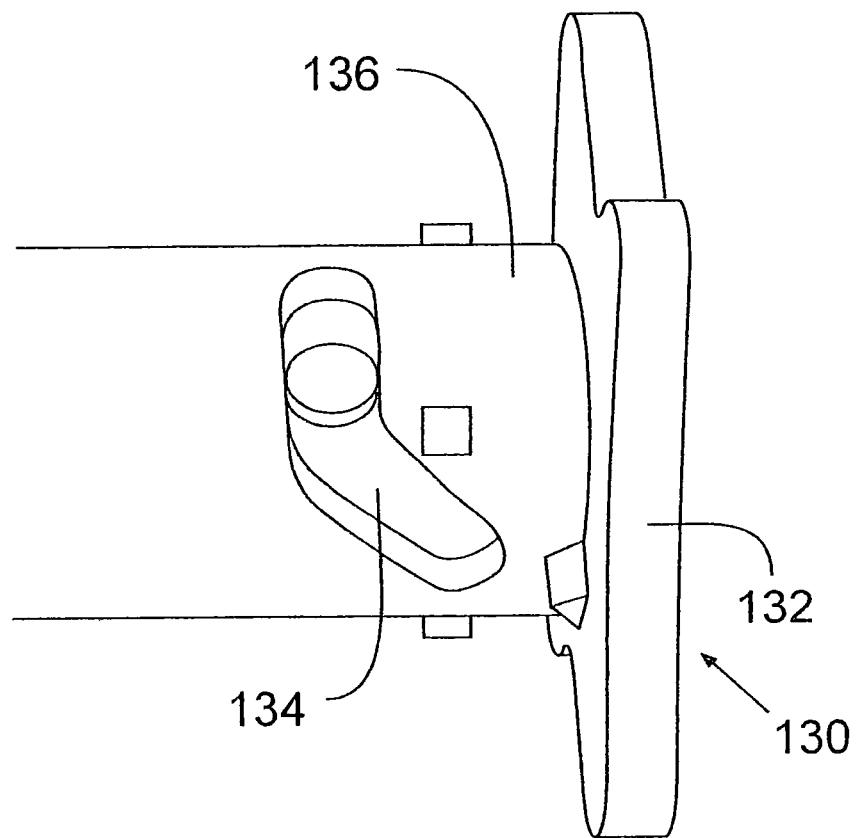
FIG. 13 shows a perspective view of a locking mechanism of the present invention in unopened condition.

As an alternative or in addition to any of the mechanisms discussed above, as shown in FIG. 13 one may use a shrink wrap indicator 130 over the device or at least the handle portion 132 of the plunger 134 and the surrounding body 136 of the device to indicate that the device is in an unopened condition.

Figure 14:
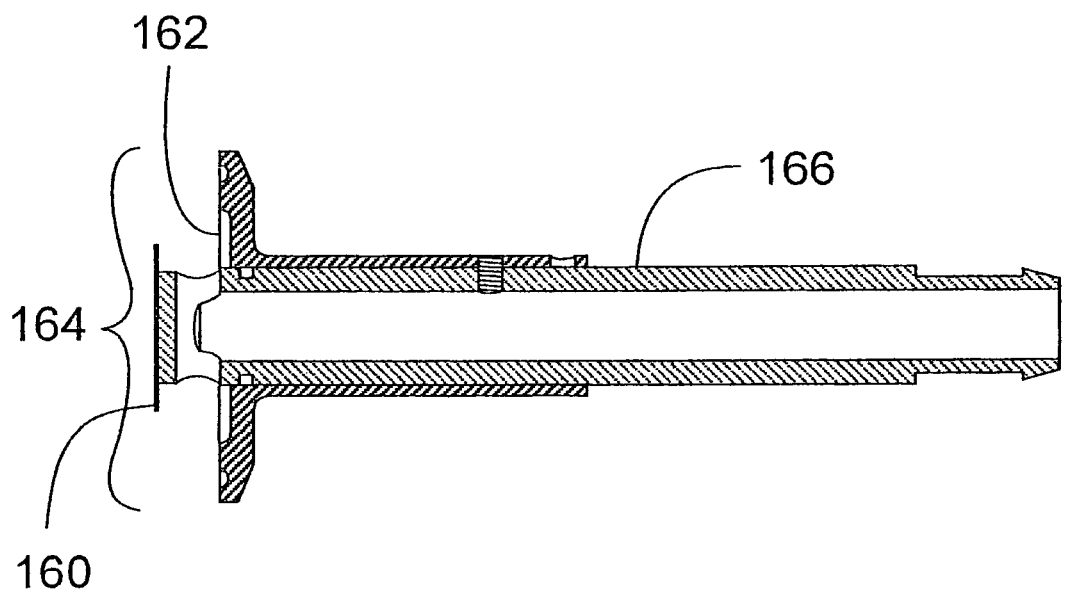
FIG. 14 shows an alternative design of the present invention.

As an alternative to the face of the device as shown in FIG. 1, one may use a foil 160, metal or plastic, such as PEI, PEEK, polysulfones, aluminum, stainless steel and the like, adhered to the body portion 162 of the face 164 and used to form the sterile seal as shown in FIG. 14. It is then pierced or penetrated by the plunger 166 to establish a fluid flow. A rubber septum in lieu of the foil could also be used. A scored surface can also be used. The foil may be adhered in a variety of manners that are well known in the art such as heat sealing, vibration welding such as ultrasonic welding, solvent bonding and through the use of adhesives such as epoxies and urethanes.

Figure 15:
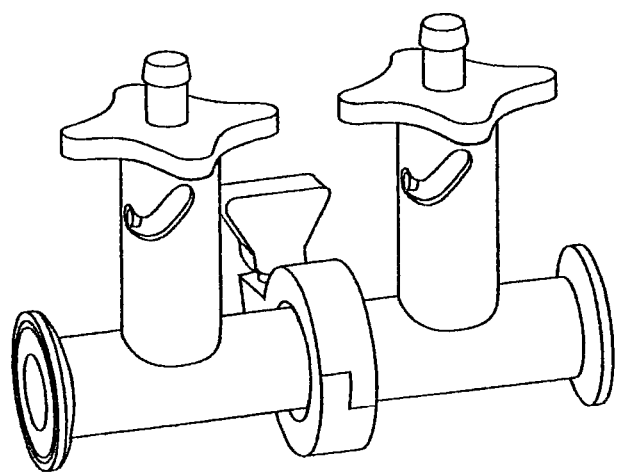
FIG. 15 shows another embodiment of the device of the present invention.

FIG. 15 shows another embodiment of the present invention. In this embodiment the body of the device is formed as an integral component of a pipe. Preferably the pipe is made of a steam resistant plastic (described below) or alternatively, it may be made of a metal such as stainless steel so long as it contains the necessary features of the present invention. The body can be formed as an arm of the piece as shown. The plunger (as shown being similar to that of FIG. 1) is then inserted into the body of the piece.

FIGS. 16 A-I show several other connectors devices that fall within the present invention. FIG. 16A is similar to the valve design of FIG. 14A. It is comprised of a body 180, and a plunger 181 contained with in a bore 182 of the housing. The plunger has a fluid channel 185 connecting it in fluid communication to the rest of the downstream side of the device and beyond. A face 183 is formed by the outermost portion of the body 180 and plunger 181. Unlike the embodiment of FIG. 1, the bore 182 is essentially linear as is the plunger 181. As shown, the device is in its open position. The plunger 181 rather than retracting into the bore 182, is extended out from the bore to expose an opening or openings 184 so as to create fluid communication between one end and the other end of the device.

Figure 16A:
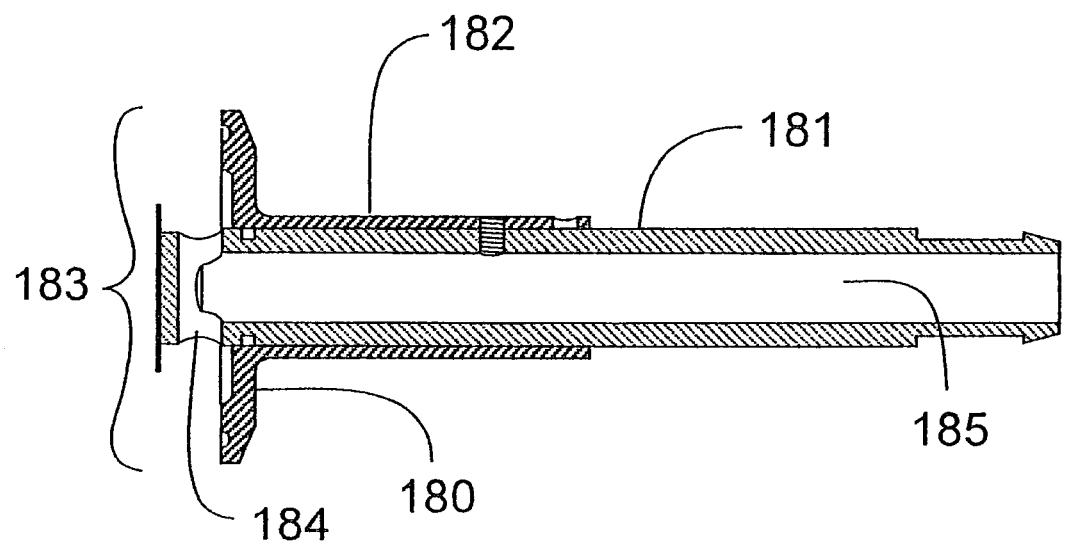
FIGS. 16A-16I show other embodiments of the device of the present invention in cross sectional view.
Figure 16B:
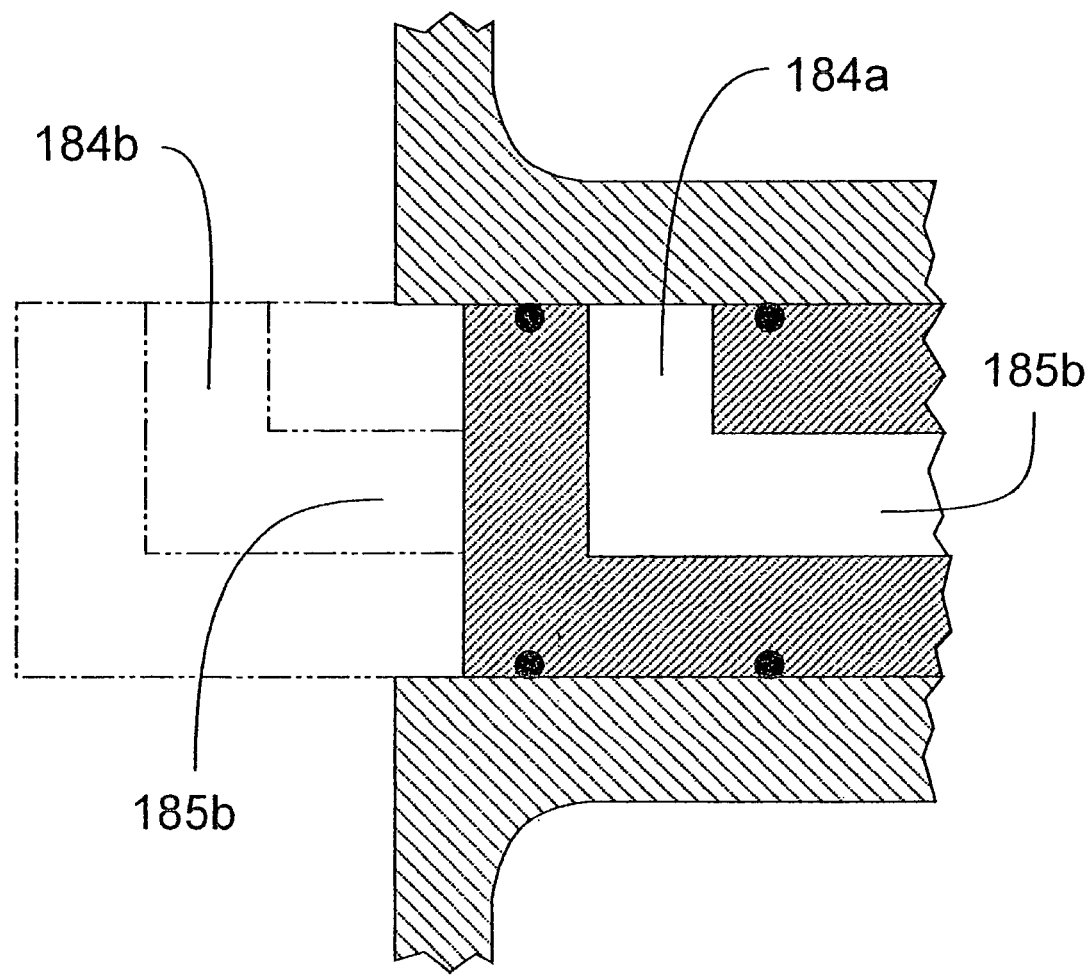

FIG. 16B shows a close up variant of the design of FIG. 16A. In this variant, the opening 184B is formed at a right angle to the fluid channel 185B only on one side of the plunger.

Figure 16C:
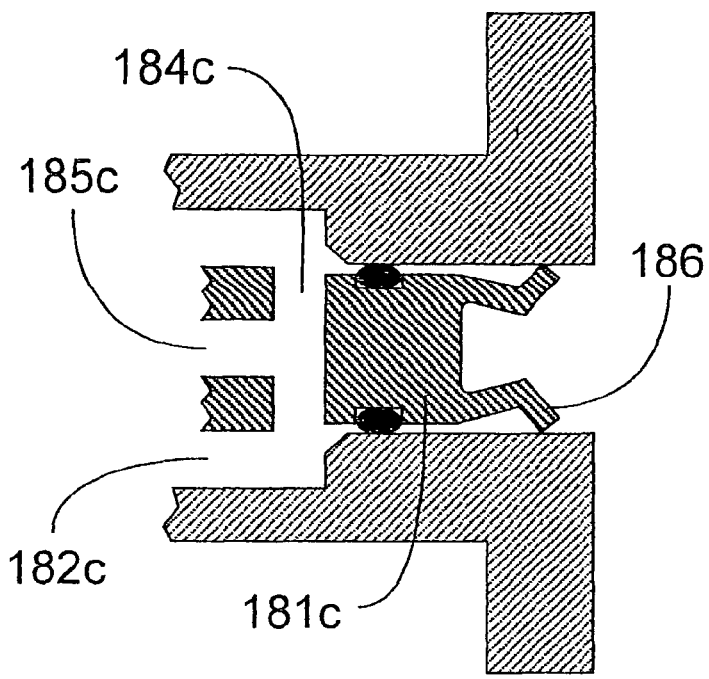
Figure 16D:
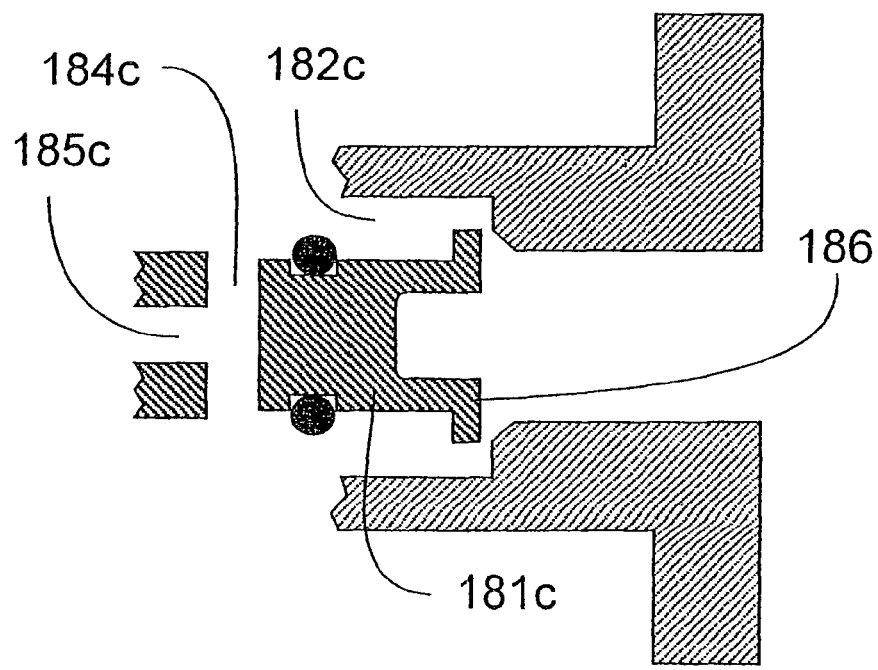

FIGS. 16C and D show a close up cross-sectional view of another embodiment. In this variant, the upstreammost portion of the plunger 181C is in the form of series of spring fingers 186. The plunger 181C is pulled back into the bore 182C to open the device as shown in FIG. 16D. Fluid then flows into the bore 182C, into openings 184C through the fluid channel 185C to the downstream component.

Figure 16E:
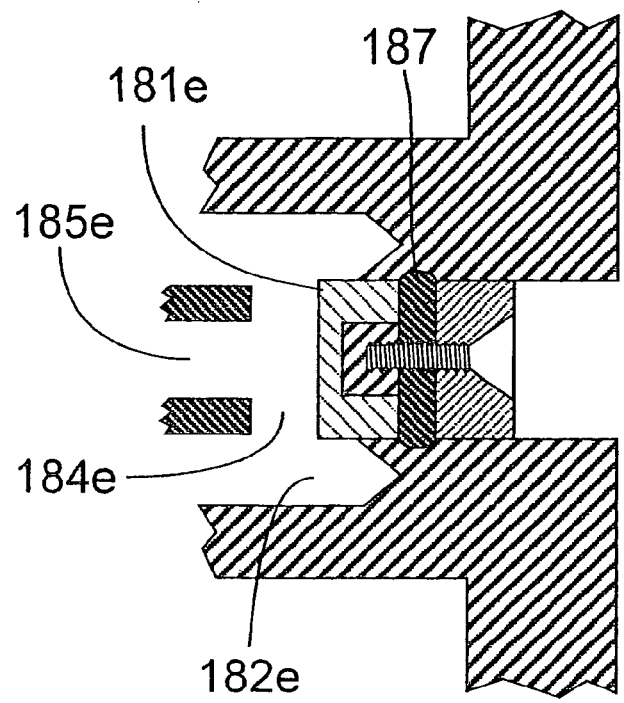
Figure 16F:
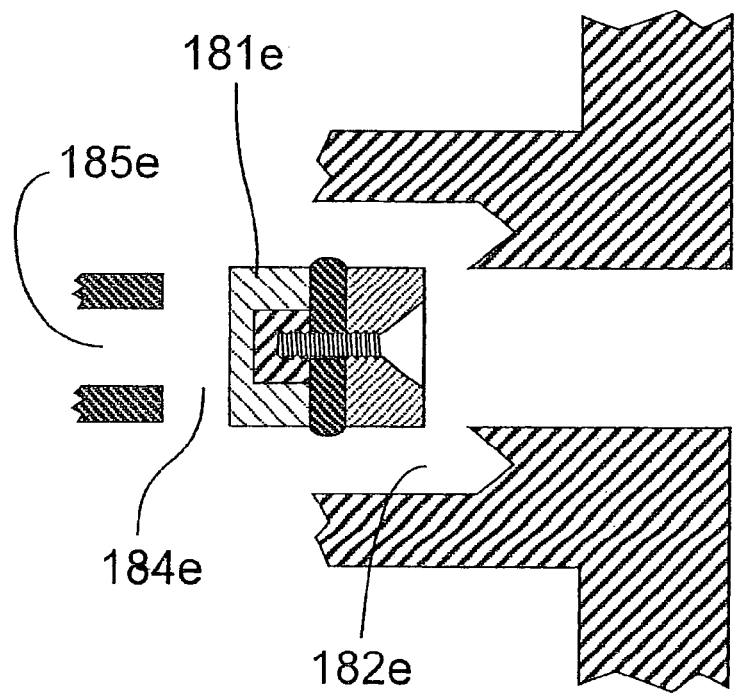
Figure 16G:
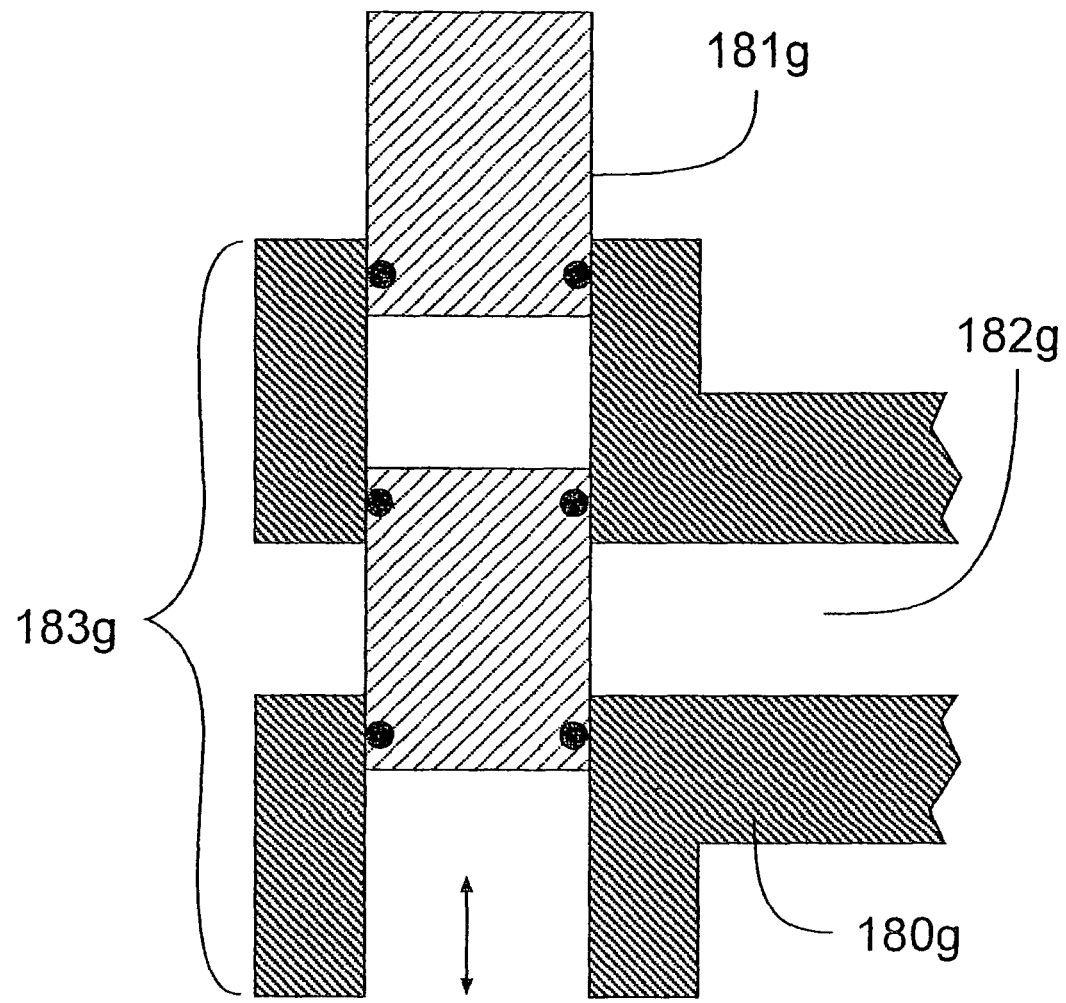
Figure 16H:
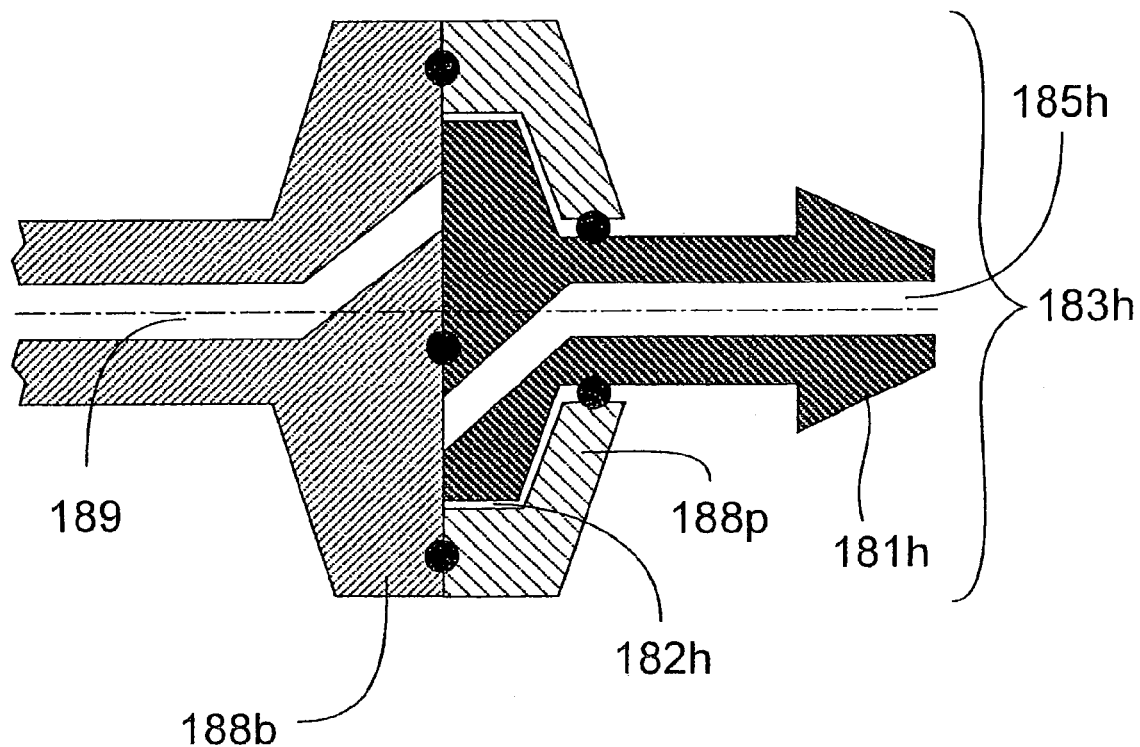
Figure 16I:
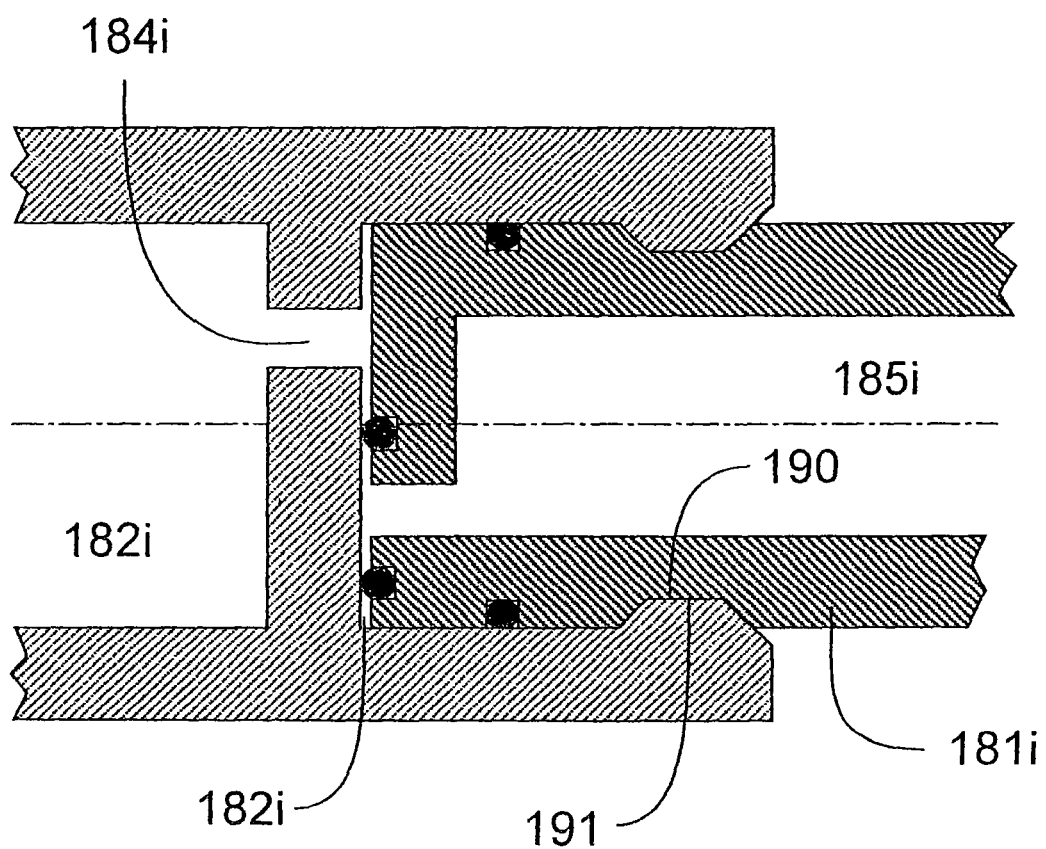

FIGS. 16E and F show a close up cross-sectional view of another embodiment. In this variant, the upstreammost portion of the plunger 181E is in the form of compression nut 187. The plunger 181E is pulled back into the bore 182E to open the device as shown in FIG. 16F. Fluid then flows into the bore 182E, into openings 184E through the fluid channel 185E to the downstream component.

FIG. 16 G shows another embodiment of the present invention. In this design, the plunger 181G is actually mounted to move laterally within the bore 182G of the housing 180G in a push/pull fashion to open and close the device. The face 183G is formed of the upstream end of the body and the plunger 181G as shown.

FIG. 16 H shows a rotatable device with the body 180H being formed of two pieces 188A and 188B. The plunger 181H is contained within a portion of the bore 182H as shown. The plunger as shown is in the closed position. The face 183H is formed by the upstreammost portions of the plunger 182H and the body portion 188B. Also as shown the upstream component is attached to the plunger 181H. As the plunger is rotated from its closed to its open position, the fluid channel 185H of the plunger aligns with a fluid channel 189 of body portion 188B to establish fluid communication through the device.

FIG. 16 I shows another variant of the rotational design. Here the Plunger 181I is retained in the bore 182I of the body 180I by a groove 190 and abutment 191. When the plunger 181I is rotated to its open position, fluid may pass through the bore 182I into the fluid channel 185I through opening 184I.

Figure 17:
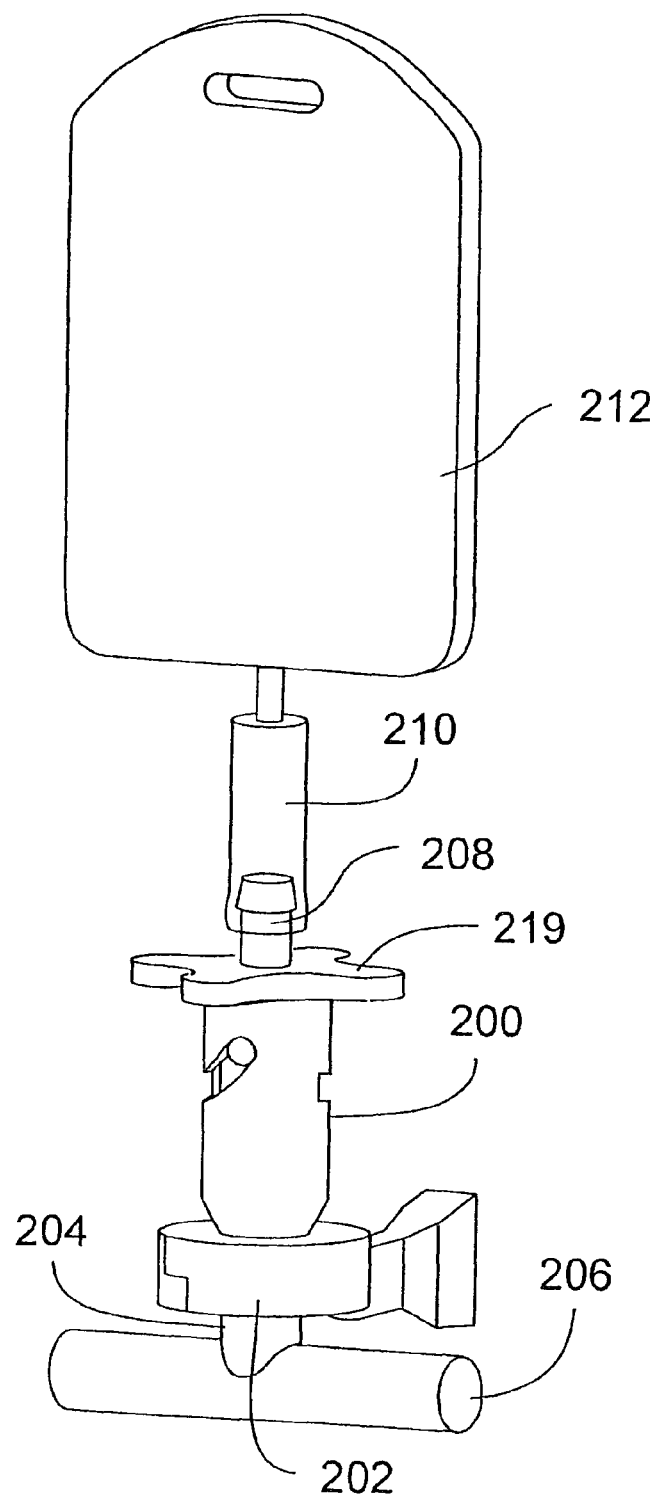
FIG. 17 shows the device of the present invention in one potential application in which there is a sterile to nonsterile connection.

FIG. 17 shows the device of the present invention in one potential application in which there is a sterile to nonsterile connection. As shown the fluid transfer device 200 of the embodiment shown in FIG. 3 is attached by its face (not shown) to a connection point 204 such as a "T" fitting on a process pipe 206 as shown. A clamp 202 holds the adjoining and mating faces (not shown, but see FIG. 3 for details of the mating assembly) of the device and the pipe 206 together in a liquid tight arrangement. The exit of the device 208 here in the form of a barb is connected to a tube 210 which in turn is connected to a collection bag 212. In use, the device 200 is in a closed position and has the tube 210 and bag 212 connected to it. The device with the tube and bag are then gamma sterilized (i.e. by gamma irradiation) or otherwise sterilized.

The device with the tube and bag is then attached to the pipe by the device face (not shown) by the clamp 202. The face is then steam sterilized along with the remainder of the system and is ready for use. When it is desired to fill the bag 212, one simply opens the device 200 by rotating the handle 214 which moves the plunger (not shown) away from the face creating an opening into the bore for the fluid to flow out the exit 208 through tube 210 and into the bag 212. Once the bag 212 is full, the handle is rotated the opposite direction to close the bore to the fluid. The bag 212 can then be closed off via a clamp or hemostat (not shown) and removed for further processing or use.

Figure 18:
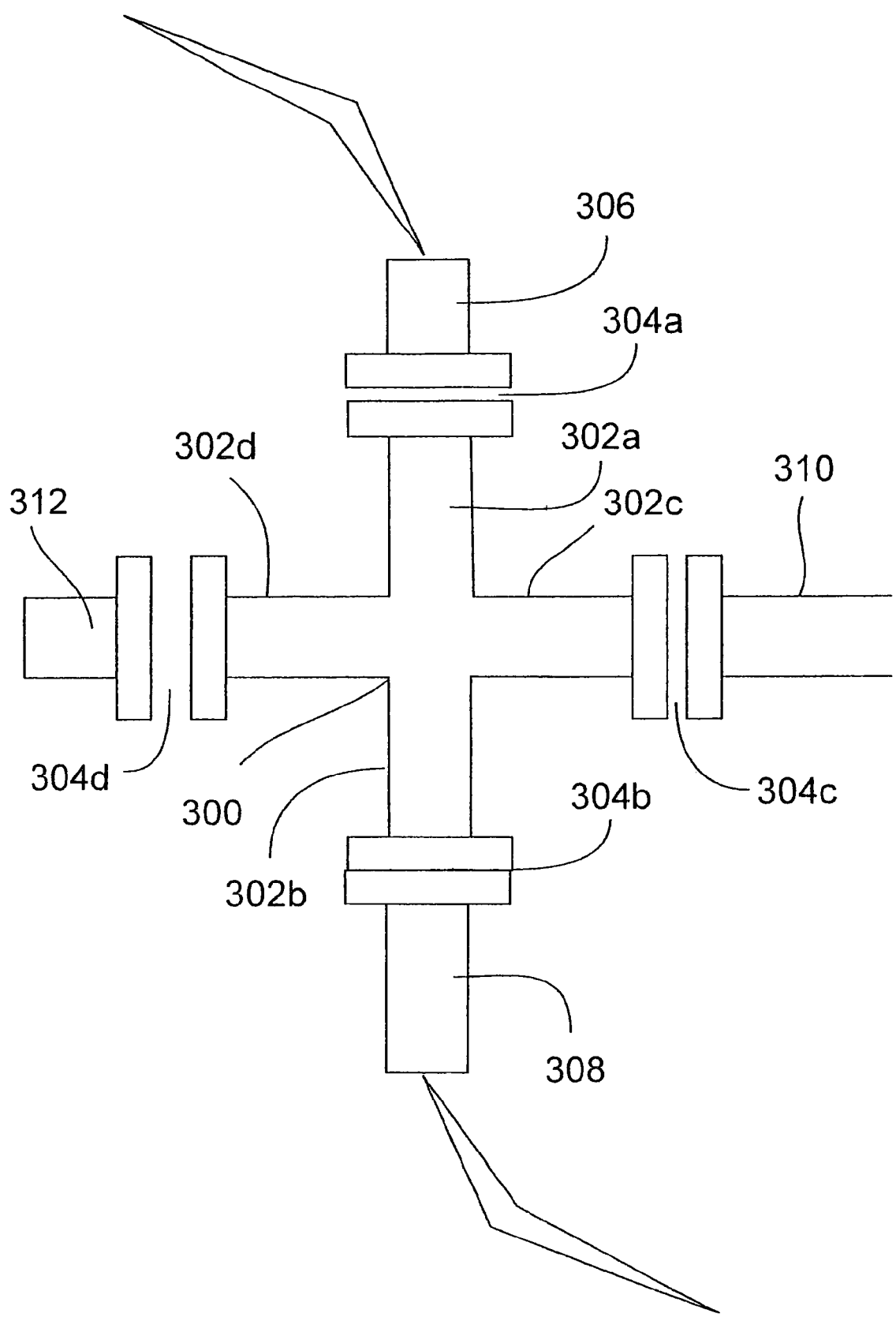
FIG. 18 shows the device of the present invention in one potential application in which there is a sterile to sterile connection.

FIG. 18 shows a system using the device of the present invention wherein two sterile devices can be connected together. As shown, one can use a connector 300 formed of four interconnecting arms 302 A, B, C and D the end of each arm 302 A, B, C and D having a mating flange 304 A, B, C and D. a first sterile transfer device 306 of the present invention in attached to arm 302A and a second device 308 is attached to a second arm 302B. A live steam line 310 is attached to arm 302C and a steam/condensate trap 312 is attached to arm 302D. Alternatively, one could attach a sterile barrier filter as taught by PCT/US01/47425, filed Dec. 3, 2001 and available from Millipore Corporation of Bedford, Mass. to arm 302D to remove the condensate after steaming.

Devices 306 and 308 are attached to other components of the system (not shown) and as with the embodiment of FIG. 14 are presterilized such as with gamma radiation before assembly the connector 300.

After assembly, steam enters through line 310 to sterilize the entire interior of connector 300 and the steamable faces of the devices 306 and 308. The steam then shut off and the steam/condensate is removed to the trap 312 which is then shut off from the connector 300. Devices 306 and 308 are then opened to form a sterile to sterile connection between them.

Other uses will be found for these devices. For example, they can be used to isolate a steam fragile component, such as some filters with steam sensitive membranes, in a process line. The filter especially in the form of a disposable capsule can be attached to the device and presterilized (such as by gamma). The device can then be connected to the line which is then steam sterilized and the device is then opened to provide fluid flow to the filter. If desired the inlet and outlet of the filter can contain such devices the outermost ends of which have the steam sterilizable face. Alternatively, a device can be attached to each end of a length of tube to form a sterile transfer pipe. Other uses can also be made of the present invention. Additionally, the connector of the present invention can be connected or actually molded into a disposable plastic container such as disposable process bag for the manufacture and transfer of biotech products. Such bags are readily available from companies such as Hyclone of Utah and Stedim of France.

The device is formed a plastic material and may be formed by machining the body and plunger assemblies and then applying the necessary seals and the like, or preferably by molding the body and the plunger separately and assembling them together with the necessary seals and other components.

The device may be made of any plastic material capable of withstanding in line steam sterilization. The temperature and pressure of such sterilization is typically about 121° C. and 1 bar above atmospheric pressure. In some instances, it may be desirable to use even harsher conditions such as 142° C. and up to 3 bar above atmospheric pressure. The body and at least the face of the plunger should be capable of withstanding these conditions. Preferably, the entire device is made of the same material and is capable of withstanding these conditions. Suitable materials for this device include but are not limited to PEI (polyetherimide), PEEK, PEK, polysulfones, polyarylsulfones, polyalkoxysulfones, polyethersulfones, polyphenyleneoxide, polyphenylenesulfide, and blends thereof. Alternatively, one can make the face portion from ceramic or metal inserts alone or that are overmolded with a plastic cover. One can also form a polymeric face with a metal outer layer using plasma coating processes.

The seals of the present invention can be made of a variety of materials typically used for making resilient seals. These materials include but are not limited to natural rubber, synthetic rubbers, such as silicone rubbers, including room temperature vulcanizable silicone rubbers, catalyzed (such as by platinum catalysts) silicone rubbers and the like, thermoplastic elastomers such as SANTOPRENE® elastomers, polyolefins such as polyethylene or polypropylene, especially those containing gas bubbles introduced either by a blowing agent or entrained gas such as carbon dioxide, PTFE resin, thermoplastic perfluoropolymer resins such as PFA and MFA resins available from Ausimont, USA of Thorofare, N.J. and E.I. DuPont de Nemours of Wilmington, Del., urethanes, especially closed cell foam urethanes, KYNAR® PVDF resin, VITON® elastomer, EPDM rubber, KALREZ resin and blends of the above.

Suitable materials for molded in place seals can be curable rubbers, such as room temperature vulcanizable silicone rubbers, thermoplastic elastomers such as SANTOPRENE® elastomers, polyolefins such as polyethylene or polypropylene, especially those containing gas bubbles introduced either by a blowing agent or entrained gas such as carbon dioxide and elastomeric fluoropolymers Other materials used in the devices should also be FDA grade components such as FDA grade silicones, PTFE resins and the like.

The present invention provides a sterile and steam sterilizable connecting device for fluid transfer. It may be single actuation (one open one close) or it may be multiple actuations with a single sterile connection (multiple openings and closings so long as the sterile connection upstream and downstream is maintained). Additionally, with the use of multiple seals or seals of long length, one is able to ensure that the sterility of the device is maintained even with multiple actuations.

What is claimed:

1. A sterile fluid transfer device comprising:
   a body having a bore formed through at least a portion of its interior, the body including a first end connectable to an upstream component;
   a port positioned downstream from the first end of the body, the port formed on a moveable plunger and being connectable to a downstream component;
   a fluid pathway through the device between the first end of the body and the port;
   the movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position; and
   a sterile barrier between the environment and at least a portion of the plunger and at least a portion of the interior of the body to enable the transfer of fluid through the fluid pathway while maintaining the sterile condition of the fluid being transferred.

2. The device of claim 1 wherein the bore is a central bore formed through a length of the body.

3. The device of claim 1 wherein the port is formed between the first end and a second end of the body.

4. The device of claim 3 wherein the port is positioned at a 90 degree angle to a length of the body.

5. The device of claim 1 wherein the body is formed of a plastic selected from the group consisting of polyetherimides (PEI), polyetheretherketone (PEEK), polyetherketone (PEK), polysulfones, polyarylsulfones, polyalkoxysulfones, polyethersulfones, polyphenylenesulfide, polyphenyleneoxide, and blends thereof.

6. The device of claim 1 wherein the body is formed of polyetherimides (PEI).

7. The device of claim 1 wherein the first end of the body is formed of a material selected from the group consisting of polyetherimides (PEI), polyetheretherketone (PEEK), polyetherketone (PEK), polysulfones, polyarylsulfones, polyalkoxysulfones, polyethersulfones, polyphenylenesulfide, polyphenyleneoxide, and blends thereof, ceramic and metal.

8. The device of claim 1 wherein the plunger is formed of a material selected from the group consisting of polyetherimides (PEI), polyetheretherketone (PEEK), polyetherketone (PEK), polysulfones, polyarylsulfones, polyalkoxysulfones, polyethersulfones, polyphenylenesulfide, polyphenyleneoxide, and blends thereof, ceramic and metal.

9. The device of claim 1 wherein the plunger is formed of polyetherimide (PEI).

10. The device of claim 1 wherein the downstream component is at least one of a bag, a sterile connector, a sanitary flange, a tube, a filter, or a pipe.

11. The device of claim 1 wherein the plunger includes one or more openings that form a fluid connection to the downstream component.

12. The device of claim 1 wherein the plunger, when in the closed position, seals off the downstream component from the upstream component.

13. The device of claim 1 wherein the body is formed of a steam resistant material.

14. The device of claim 1 wherein the surface formed by the first end of the body and the first end of the plunger is formed of metal.

15. The device of claim 1 wherein the body is formed of a plastic.

16. The device of claim 1 wherein the steamable surface further comprises a seal.

17. The device of claim 1 wherein the sterile barrier further comprises at least one seal.

18. The device of claim 17 wherein the sterile barrier further comprises at least three seals.

19. The device of claim 17 wherein the at least one seal is a gland seal.

20. A sterile fluid transfer device comprising:
   a body having a bore formed through at least a portion of its interior, the body including a first end connectable to an upstream component;
   a filter in fluid communication with the bore, the filter having a steam sensitive membrane;
   a fluid pathway through the device;
   a movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position;
   a handle for moving the plunger within the bore; and
   a sterile barrier between the environment and at least a portion of the plunger and at least a portion of the interior of the body to enable transfer of fluid through the fluid pathway while maintaining the sterile condition of the fluid being transferred.

21. The device of claim 1, wherein the bore comprises a first bore section proximate the first end and having a first diameter, a second bore section having a second diameter larger than the first diameter and downstream from the first bore section, and a transition bore section between the first and second bore sections, and wherein the plunger has a shape corresponding to that of the bore.

22. A sterile fluid transfer device comprising:
   a body having a bore formed through at least a portion of its interior, the body including a first end connectable to an upstream component;
   a port connectable to a downstream component;

a fluid pathway through the device between the first end of the body and the port;

a movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position;

a handle for moving the plunger within the bore; and a sterile barrier between the environment and at least a portion of the plunger and at least a portion of the interior of the body to enable the transfer of fluid through the fluid pathway while maintaining the sterile condition of the fluid being transferred.

23. A sterile fluid transfer device comprising:

a body having a bore formed through at least a portion of its interior, the body including a first end connectable to an upstream component;

a port formed on a portion of the body downstream of the first end of the body, the port being connectable to a downstream component;

a fluid pathway through the device between the first end of the body and the port;

a movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position;

a handle for moving the plunger within the bore; and a sterile barrier between the environment and at least a portion of the plunger and at least a portion of the interior of the body to enable the transfer of fluid through the fluid pathway while maintaining the sterile condition of the fluid being transferred.

24. A sterile fluid transfer device comprising:

a body having a bore formed through at least a portion of its interior, the body including a first end connectable to an upstream component;

a port positioned downstream from the first end of the body, the port being connectable to a downstream component;

a fluid pathway through the device between the first end of the body and the port;

a movable plunger contained within the bore, the plunger having a first end and being movable within the bore between a closed position and an open position, the plunger enabling a transfer of fluid through the fluid pathway when the plunger is in the open position;

a handle for moving the plunger within the bore; and a sterile barrier between the environment and at least a portion of the plunger and at least a portion of the interior of the body to enable the transfer of fluid through the fluid pathway while maintaining the sterile condition of the fluid being transferred.

25. A sterile fluid transfer device comprising:

a body having a bore formed through at least a portion of its interior, the body including a first end connectable to an upstream component;

a port positioned downstream from the first end of the body, the port being connectable to a downstream component;

a fluid pathway through the device between the first end of the body and the port;

a movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position;

a handle for moving the plunger within the bore; and a sterile barrier between the environment and at least a portion of the plunger and at least a portion of the interior of the body to enable the transfer of fluid through the fluid pathway while maintaining the sterile condition of the fluid being transferred through at least one actuation.

26. The device of claim 25 wherein the sterile condition is maintained through multiple actuations.

27. A sterile fluid transfer device comprising:

a body having a bore formed through at least a portion of its interior, the body including a first end connectable to an upstream component;

a port positioned downstream from the first end of the body, the port being connectable to a downstream component;

a fluid pathway through the device between the first end of the body and the port;

a movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position; and a sterile barrier between the environment and at least a portion of the plunger and at least a portion of the interior of the body to enable the transfer of fluid through the fluid pathway while maintaining the sterile condition of the fluid being transferred, the sterile barrier comprising at least three seals.

28. A sterile fluid transfer device comprising:

a body having a bore formed through at least a portion of its interior, the body including a first end connectable to an upstream component;

a port positioned downstream from the first end of the body, the port being connectable to a downstream component;

a fluid pathway through the device between the first end of the body and the port;

a movable plunger contained within the bore, the plunger having a first end and being movable within the bore between a closed position and an open position, the first end of the plunger and at least the first end of the body forming a steamable surface when the plunger is in the closed position, and the plunger enabling a transfer of fluid through the fluid pathway when the plunger is in the open position; and a sterile barrier between the environment and at least a portion of the plunger and at least a portion of the interior of the body to enable the transfer of fluid through the fluid pathway while maintaining the sterile condition of the fluid being transferred, the sterile barrier comprising at least one seal wherein the at least one seal is a gland seal.

* * * * *